(12) United States Patent
Corlett

(10) Patent No.: US 11,908,577 B2
(45) Date of Patent: Feb. 20, 2024

(54) TELEMEDICINE PLATFORM INCLUDING VIRTUAL ASSISTANCE

(71) Applicant: Health Science Partners LLC, San Diego, CA (US)

(72) Inventor: Scott Corlett, San Diego, CA (US)

(73) Assignee: HEALTH SCIENCE PARTNERS LLC, San Diego, CA (US)

(*) Notice: Subject to any disclaimer, the term of this patent is extended or adjusted under 35 U.S.C. 154(b) by 0 days.

(21) Appl. No.: 17/871,475

(22) Filed: Jul. 22, 2022

(65) Prior Publication Data
US 2024/0029879 A1 Jan. 25, 2024

(51) Int. Cl.
*G16H 40/67* (2018.01)
*G16H 80/00* (2018.01)

(52) U.S. Cl.
CPC ............ *G16H 40/67* (2018.01); *G16H 80/00* (2018.01)

(58) Field of Classification Search
USPC .......................................................... 705/2
See application file for complete search history.

(56) References Cited

U.S. PATENT DOCUMENTS

| | | |
|---|---|---|
| 7,098,788 B2 | 8/2006 | Giraldo et al. |
| 7,895,061 B2 | 2/2011 | Schoenberg |
| 7,937,275 B2 | 5/2011 | Schoenberg |
| 8,352,245 B1 | 1/2013 | Lloyd |
| 8,504,382 B2 | 8/2013 | Schoenberg |
| 8,515,776 B2 | 8/2013 | Schoenberg |
| 8,600,773 B2 | 12/2013 | Schoenberg |
| 9,971,873 B2 | 5/2018 | Schoenberg |
| 10,510,449 B1* | 12/2019 | Reicher .................. G16H 15/00 |
| 10,977,522 B2 | 4/2021 | Anushiravani et al. |
| 11,023,990 B2 | 6/2021 | Choksi et al. |
| 11,195,617 B1 | 12/2021 | Singh et al. |
| 11,205,510 B2 | 12/2021 | Ross et al. |
| 11,289,189 B2 | 3/2022 | Eberting |

(Continued)

OTHER PUBLICATIONS

Monteiro, S. (2015). An intelligent telemedicine platform with cognitive support for chronic care management (Order No. 10187000). Available from ProQuest Dissertations and Theses Professional. (1861733742). Retrieved from https://dialog.proquest.com/professional/docview/1861733742?accountid=131444 (Year: 2015).*

(Continued)

*Primary Examiner* — Christopher L Gilligan
*Assistant Examiner* — Bennett Stephen Erickson
(74) *Attorney, Agent, or Firm* — NEO IP

(57) ABSTRACT

A telemedicine platform utilizes artificial intelligence to match patients with practitioners. The platform includes a virtual assistant operable to automatically generate responses to a patient using machine learning in order to further identify details regarding the patient's symptoms and needs. The virtual assistant includes a digitally generated human face that automatically adapts mouth-movements and facial expressions to match the automatically generated responses in order to provide a feeling of interacting with a human assistant. The platform includes a patient interface, for identifying physicians and scheduling appointments, a practitioner interface, for managing patients and scheduling issues, and an administrator interface, for managing a larger practice of multiple practitioners.

20 Claims, 31 Drawing Sheets

(56) References Cited

U.S. PATENT DOCUMENTS

| | | | |
|---|---|---|---|
| 11,328,215 B2 | 5/2022 | Douglas et al. | |
| 2001/0039504 A1* | 11/2001 | Linberg | G06Q 10/10 |
| | | | 705/3 |
| 2015/0081338 A1* | 3/2015 | Lai | G05D 1/0088 |
| | | | 705/2 |
| 2015/0178459 A1* | 6/2015 | Wortman | G16H 40/67 |
| | | | 705/2 |
| 2015/0302536 A1* | 10/2015 | Wahl | G06Q 50/00 |
| | | | 705/2 |
| 2016/0098542 A1 | 4/2016 | Costantini et al. | |
| 2020/0151519 A1 | 5/2020 | Anushiravani et al. | |
| 2020/0243194 A1 | 7/2020 | Epstein | |
| 2020/0357520 A1 | 11/2020 | Fujimoto et al. | |
| 2020/0381105 A1 | 12/2020 | Bernard et al. | |
| 2021/0098088 A1 | 4/2021 | Hashimoto et al. | |
| 2021/0209249 A1* | 7/2021 | Hoffer | G06F 21/6245 |
| 2021/0233658 A1 | 7/2021 | Assel et al. | |
| 2021/0295996 A1 | 9/2021 | Goetz et al. | |
| 2021/0304896 A1 | 9/2021 | Chen et al. | |
| 2021/0319914 A1* | 10/2021 | Roh | G16H 40/67 |
| 2021/0386364 A1 | 12/2021 | Downing | |
| 2021/0398679 A1 | 12/2021 | Bari et al. | |
| 2022/0000351 A1 | 1/2022 | Yamada et al. | |
| 2022/0076851 A1* | 3/2022 | Kamangar | G06Q 30/0633 |
| 2022/0215970 A1* | 7/2022 | Trpkovski | G07C 9/00904 |
| 2022/0240779 A1* | 8/2022 | Peyman | G16H 30/20 |
| 2022/0270747 A1* | 8/2022 | Van Zon | G16H 40/20 |

OTHER PUBLICATIONS

MayaMD https://www.mayamd.ai/.

* cited by examiner

15 Todays Appointment

View All

| Patient Name | Gender | Appointment Time | Mobile Number | Status | Actions |
|---|---|---|---|---|---|
| John Joseph | Male | 10:00 AM - 10:30 AM | (123) 456-7890 | Upcoming | ... |
| Mary Farmer | Female | 10:40 AM - 11:10 AM | (123) 456-7891 | Upcoming | Create Prescription / Edit Appointment / Cancel Appointment |
| Marianne Mencia | Female | 11:20 AM - 11:55 AM | (123) 456-7892 | Upcoming | ... |
| LeAnn Barry | Female | 12:15 PM - 12:45 PM | (123) 456-7893 | Upcoming | ... |
| Jerry Hendricks | Male | 01:00 PM - 01:30 PM | (123) 456-7894 | Upcoming | ... |

FIG. 3

Manage Profile

| | | |
|---|---|---|
| First Name | Last Name | Date of Birth | Gender |
| Alex | Walters | 08/01/1988 | Female |
| Language | Mobile Number | Email Address | |
| English | 845-494-5555 | sam_billings@yopmail.com | |
| Designation | Years of Experience | Registration Number | Department |
| Doctor | 5 Years | 112647 | Laboratory |
| Practice Area | | Specialization | |
| Vaccination, Test | | BSc Nursing | |
| Qualifications | | | |
| BAMS | | | |

About
Enter short description about yourself

Account Verification

Search by name, email or phone

Sort by Status ⌄   Show 50 ⌄

| Practitioner Name | Department | Mobile Number | Email | Status | Actions |
|---|---|---|---|---|---|
| Alice Waters | General Physician | (123) 456-7890 | awaters@gmail.com | Review | Verify |
| Shaun Peters | Pediatricians | (123) 456-7880 | speters@gmail.com | Review | Verify |
| Carlita Velasquez | Cardiologist | (123) 456-7881 | cvelasquez@gmail.com | Review | Verify |
| Clio Miranda | Dermatologists | (123) 456-7882 | cmiranda@gmail.com | Pending | |
| Anna Watkins | ENT Specialist | (123) 456-7883 | awatkins@gmail.com | Pending | |
| Mark Hamilton | General Physician | (123) 456-7884 | mhamilton@gmail.com | Review | Verify |
| Lyra Kinsky | Cardiologist | (123) 456-7885 | lkinsky@gmail.com | Review | Verify |
| Sarah Shoreland | General Physician | (123) 456-7886 | sshoreland@gmail.com | Pending | |
| Francisco Aliyah | Cardiologist | (123) 456-7887 | faliyah@gmail.com | Review | Verify |
| Hortense Miller | Cardiologist | (123) 456-7888 | hmiller@gmail.com | Review | Verify |

Showing 1 to 10 of 47 users    1 2 3 4 5 Next

MEDA
- Dashboard
- Patient Management
- Practitioner Management
- Account Verification
- Notifications Manuel Richards

TELEMEDICINE PLATFORM INCLUDING VIRTUAL ASSISTANCE

BACKGROUND OF THE INVENTION

1. Field of the Invention

The present invention relates to a telemedicine platform, and more specifically to telemedicine platforms including virtual physicians.

2. Description of the Prior Art

It is generally known in the prior art to provide platforms for facilitating remote communication between patients and physicians, in a field known as telemedicine. Telemedicine platforms such as CHIRON HEALTH and DOXY.ME focus on providing HIPAA-compliant platforms for video conferencing with physicians and managing schedules, including providing automatic appointment reminders. These platforms also commonly facilitate the sharing of electronic health records and provide systems for managing billing.

Important to some existing platforms, such as EVISIT, is the ability to customize and automate workflow processes to match individual physicians' organizational practices. For other applications, such as MEDICI, the systems divide operations into cases associated with specific patients assigned to particular physicians, allowing additional physicians to be brought in to provide second opinions. Platforms such as SIMPLEPRACTICE have attempted to provide other features in addition to traditional telemedicine features, such as systems for submitting and reconciling insurance claims.

Some telemedicine platforms focus on providing communication means for existing patient-physician relationships, while others, such as THERA-LINK focus on providing means for patients to search for new providers, or group therapy sessions.

Prior art patent documents include the following:

U.S. Pat. No. 7,098,788 for Remote surveillance and assisted care using a mobile communication device by inventors Giraldo et al., filed Jul. 12, 2004 and issued Aug. 29, 2006, describes a method of remote surveillance and assisted care using a mobile communication device including determining a location of a user. The method can also include adjusting at least one camera according to the location, and capturing an image of an area around the location. Further, the method can include transmitting the image to a remote information processing system.

U.S. Pat. No. 11,289,189 for Systems and methods for auto-generation of telemedicine clinics by inventor Eberting, filed Aug. 8, 2019 and issued Mar. 29, 2022, describes systems and methods for automatically generating telemedicine platforms for providers. A marketplace of healthcare services and associated pricing and other terms is made available to employers, individuals, and/or health insurance companies. Employers and/or health insurance companies can select a subset of options from the marketplace to create a customizable sub-marketplace of healthcare services to offer to their employees or insureds. Providers may modify their offerings in the marketplace to fit within guidelines established by the employers or health insurance companies to be automatically included in the sub-marketplace of healthcare services.

U.S. Pat. No. 8,352,245 for Adjusting language models by inventor Lloyd, filed Mar. 31, 2011 and issued Jan. 8, 2013, describes methods, systems, and apparatuses, including computer programs encoded on a computer storage medium, for adjusting language models. In one aspect, a method includes accessing audio data. Information that indicates a first context is accessed, the first context being associated with the audio data. At least one term is accessed. Information that indicates a second context is accessed, the second context being associated with the term. A similarity score is determined that indicates a degree of similarity between the second context and the first context. A language model is adjusted based on the accessed term and the determined similarity score to generate an adjusted language model. Speech recognition is performed on the audio data using the adjusted language model to select one or more candidate transcriptions for a portion of the audio data.

U.S. Pat. No. 11,205,510 for Systems and methods for visualizing and managing telepresence devices in healthcare networks by inventors Ross et al., filed Feb. 1, 2016 and issued Dec. 21, 2021, describes systems and methods for visualizing, analyzing, and managing telepresence devices operating in a telepresence network of healthcare facilities. The visualization and management system for telepresence devices may display a first viewing level that includes a geographical representation of the location of various telepresence devices. A user may selectively view a global view of all telepresence devices, telepresence devices within a particular region, and/or the details of a particular telepresence device. A user may also access a viewing level of a network of healthcare facilities. The user may view, analyze, and/or manage the healthcare network, telepresence device network, individual telepresence devices, connection rules, and/or other aspects of the healthcare network using the geographical visualization and management tool.

U.S. Pat. No. 11,023,990 for Programmatically providing information in connection with location-based services to service providers by inventors Choksi et al., filed Apr. 15, 2016 and issued Jun. 1, 2021, describes a system and method of providing information in connection with one or more services on a computing device. The system can receive data in connection with a location-based service from a remote system and can programmatically display information about the service on or as part of a user interface of the service application. A system can dynamically display content to instruct a user of the computing device to go to a particular location and to perform a particular task associated with the service based on the user's current condition.

U.S. Pat. No. 11,195,617 for Intelligent triaging engine by inventors Singh et al., filed Nov. 10, 2016 and issued Dec. 7, 2021, describes a method for intelligently triaging patients. The computer-implemented may diagnose a patient based up a received set of medical symptoms. In response, to the diagnosis, a filterable and/sortable list of healthcare service recommendations may be generated. The list of healthcare services may be generated based upon an analysis of a plurality of user data. Each recommendation on the list of healthcare service recommendations may correspond to a plurality of metadata describing the associated healthcare service. When a user selects a particular healthcare service from the list of healthcare service recommendations, the method may include interconnecting a client device with a computing system associated with the particular healthcare service.

U.S. Pat. No. 7,937,275 for Identifying clinical trial candidates by inventor Schoenberg, filed May 8, 2008 and issued May 3, 2011, describes identifying one or more clinical study candidates by consolidating health care information for a consumer, applying the consumer's health care information to a rules engine, identifying a consumer as eligible to participate in one or more clinical studies, and presenting an opportunity to participate in the study to the consumer.

U.S. Pat. No. 8,515,776 for Medical listener by inventor Schoenberg, filed Apr. 15, 2011 and issued Aug. 20, 2013, describes an engagement brokered between a consumer and a medical service provider; electronic text of a real-time, text-based communication between the medical service provider and the consumer is monitored during the engagement; the electronic text is analyzed for a triggering event related to at least one of medical diagnosis and medical treatment; the triggering event is detected in the electronic text; and medical information is provided to the medical service provider via a user interface in response to the triggering event.

U.S. Pat. No. 9,971,873 for Connecting consumers with service providers by inventor Schoenberg, filed Aug. 9, 2017 and issued May 15, 2018, describes a request received from a consumer of services to consult with a service provider having a service provider profile that satisfies at least some attributes in a set of attributes that define a suitable service provider; an available service provider satisfying at least some of the attributes in the set of attributes is identified; and a communication channel to establish a communication between the consumer of services and the identified service provider.

U.S. Pat. No. 7,895,061 for Auctioning Provider Prices by inventor Schoenberg, filed Mar. 31, 2008 and issued Feb. 22, 2011, describes a computer-implemented method including receiving, at a computer-based system for connecting consumers with providers in real time over the Internet, requested compensation amounts from a plurality of providers. The method also includes displaying a price associated with consulting with a particular provider to a consumer on a user interface, the price being based at least in part on the requested compensation amount received from the provider.

U.S. Pat. No. 8,600,773 for Tracking The Availability Of Service Providers Across Multiple Platforms by inventor Schoenberg, filed Oct. 27, 2010 and issued Dec. 3, 2013, describes tracking the availability of service providers across one or more service provider networks. A status change of the service provider is identified on one or more of the service provider networks and the other service provider networks associated with the service provider is sent data indicating the changed status of the service provider.

U.S. Pat. No. 8,504,382 for Identifying trusted providers by inventor Schoenberg, filed Feb. 21, 2008 and issued Aug. 6, 2013, describes a computer-implemented method including receiving a request from a consumer associated with a first medical service provider to engage in real time with a medical service provider over the Internet. The method also includes in response to the received request, displaying a list of medical service providers to the consumer on a user interface. The method also includes providing an indicator associated with a particular medical service provider in the list of medical service providers if the particular medical service provider is a trusted medical service provider identified by the first medical service provider.

US Patent Publication No. 2021/0386364 for Automated health review system by inventor Downing, filed Jun. 12, 2022 and published Dec. 16, 2021, describes a system and method for providing health care diagnosis, and more specifically, to a system and method for providing automated health condition review and diagnosis with testing recommendations. The system includes a condition analyzer server coupled to online prior medical records sources, a current treating facility processor for generating a set of current patient data, the current patient data comprises observations, conditions, vital signs, and complaints, and a data storage device containing one or more sets of one or more predetermined criteria from reference sources and record results. The condition analyzer server return a report containing recommendations potential diagnosis, additional testing recommendations, and reference source materials utilized in generating the potential diagnosis, and additional testing recommendations to the current treating facility.

US Patent Publication No. 2021/0304896 for Systems and methods for medical diagnosis by inventors Chen et al., filed Mar. 31, 2021 and published Sep. 30, 2021, describes a method including generating at least one first segmentation image and at least one second segmentation image based on the target image. Each of the at least one first segmentation image may indicate one of the at least one target region of the subject. Each of the at least one second segmentation image may indicate a lesion region of one of the at least one target region. The method may also include determining first feature information relating to the at least one lesion region and the at least one target region based on the at least one first segmentation image and the at least one second segmentation image. The method may further include generating a diagnosis result with respect to the subject based on the first feature information.

US Patent Publication No. 2021/0295996 for Machine learning models for diagnosis suspecting by inventors Goetz et al., filed Mar. 23, 2020 and published Sep. 23, 2021, describes methods and systems for machine learning models utilized for diagnosis suspecting. These methods and systems utilize machine learning models may be trained to diagnose diseases or conditions. The models may be trained with data from disparate sources that are aggregated and formatted to be utilized in these models.

US Patent Publication No. 2021/0233658 for Identifying Relevant Medical Data for Facilitating Accurate Medical Diagnosis by inventors Van Assel et al., filed Jan. 23, 2020 and published Jul. 29, 2021, describes a computer-implemented method for medical diagnosis, comprising: receiving a user input from a user, the user input comprising an input symptom; determining a measure of relevance of a plurality of items of medical data to the user input, wherein the plurality of items of medical data are items of medical data for which information associated with the user is stored; determining whether to include the stored information corresponding to an item of medical data in a first set of information, based on the measure of relevance for the item of medical data; providing the user input and the first set of information as an input to a model, the model being configured to output a probability of the user having a disease; and outputting a diagnosis based on the probability of the user having a disease.

US Patent Publication No. 2021/0098088 for Diagnosis/treatment assisting apparatus and diagnosis/treatment assisting system by inventors Hashimoto et al., filed Sep. 21, 2020 and published Apr. 1, 2021, describes a diagnosis assisting apparatus including a processing circuit and a display circuit. The processing circuit is configured to obtain a first question represented by a question from a patient to a medical doctor. The processing circuit is configured to analyze content of the obtained first question. The processing circuit is configured to convert the first question into a second question having equivalent content and using a different expression, on the basis of a result of the analysis. The display circuit is configured to display the second question.

US Patent Publication No. 2020/0381105 for Medical scan diagnosing system by inventors Bernard et al., filed Aug. 20, 2020 and published Dec. 3, 2020, describes a medical scan diagnosing system operable to receive a medical scan. Diagnosis data of the medical scan is generated by performing a medical scan inference function on the medical scan. The first medical scan is transmitted to a first client device associated with a user of the medical scan diagnosing system in response to the diagnosis data indicating that the medical scan corresponds to a non-normal diagnosis. The medical scan is displayed to the user via an interactive interface displayed by a display device corresponding to the first client device. Review data is received from the first client device, where the review data is generated by the first client device in response to a prompt via the interactive interface. Updated diagnosis data is generated based on the review data. The updated diagnosis data is transmitted to a second client device associated with a requesting entity.

US Patent Publication No. 2020/0243194 for Computerized Medical Diagnostic and Treatment Guidance by inventor Epstein, filed Jan. 23, 2020 and published Jul. 30, 2020, describes a method and system for aiding in the diagnosis and treatment of medical and health conditions. In some embodiments, a risk profiler analyzes population incidence statistics with test results to populate an interactive simulation and decision engine. Further embodiments produce treatment betting tables. In some embodiments, diagnosis fact boxes are produced. Users, such as clinicians and patients, interact with the simulation and decision engine to explore different diagnosis possibilities and treatment options, with feedback showing the statistical likelihoods and consequences of the possibilities.

US Patent Publication No. 2020/0151519 for Intelligent Health Monitoring by inventors Anushiravani et al., filed Nov. 11, 2019 and published May 14, 2020, describes embodiments for health assessment and diagnosis implemented in an artificial intelligence (AI) system. The AI system takes as input information from a multitude of sensors measuring different biomarkers in a continuous or intermittent fashion. The proposed techniques address the unique challenges encountered in implementing such an AI system.

US Patent Publication No. 2016/0098542 for Medical diagnosis and treatment support apparatus, system, and method by inventors Constantini et al., filed Sep. 30, 2015 and published Apr. 7, 2016, describes an automated medical computer logic apparatus, which can provide automated medical diagnosis and treatment support to HCPs and patients. A patient can indicate a chief complaint such as chest pain, ear discomfort, a rash, or the like. A rules engine can include clinical modules and a module selector. The module selector can receive the chief complaint and select a particular clinical module. An evaluator logic section can receive and process the selected clinical module. Based on the selected clinical module, the evaluator logic section can cause a dynamic interview to be conducted with the patient, and can map individual question responses to various possible diagnoses, indicating how much each diagnosis should be weighted. The evaluator logic section can suggest treatment options. The automated medical computer logic apparatus can analyze patient responses and automatically generate a customized treatment plan, an automated chart note narrative, a detailed clinical summary, and/or patient education information.

U.S. Pat. No. 11,328,215 for Computer implemented determination method and system by inventors Douglas et al., filed Feb. 15, 2019 and issued May 10, 2022, describes methods for providing a computer implemented medical diagnosis. In one aspect, a method includes receiving an input from a user comprising at least one symptom of the user, and providing the at least one symptom as an input to a medical model. The method also includes deriving estimates of the probability of the user having a disease from the discriminative model, inputting the estimates to the inference engine, performing approximate inference on the probabilistic graphical model to obtain a prediction of the probability that the user has that disease, and outputting the probability of the user having the disease for display by a display device.

U.S. Pat. No. 10,977,522 for Stimuli for symptom detection by inventors Anushiravani et al., filed Nov. 11, 2019 and issued Apr. 13, 2021, describes embodiments for health assessment and diagnosis implemented in an artificial intelligence (AI) system. In an embodiment, a method comprises: obtaining, using one or more processors of a device, a speech sample from a user uttering a first sentence; processing the speech sample through a neural network to predict a first set of one or more disease-related symptoms of the user; and generating, using the one or more processors, a second sentence to predict a second set of one or more disease-related symptoms or confirm the first set of disease-related symptoms.

US Patent Publication No. 2022/0000351 for Control apparatus, diagnosis support method, and recording medium by inventors Yamada et al., filed Sep. 16, 2021 and published Jan. 6, 2022, describes a diagnosis support apparatus including a processor including at least one piece of hardware. The processor identifies, based on physical information including one or more kinds of information capable of estimating a state of a diagnosis target organ of a subject, one abnormal symptom appearing in the diagnosis target organ, performs, as lesion extraction processing for extracting a lesion candidate region from an endoscopic image, different processing specialized for each abnormal symptom that appears in the diagnosis target organ, and performs the lesion extraction processing corresponding to the identified one abnormal symptom.

US Patent Publication No. 2021/0398679 for Systems and methods for using multiscale data for variable, pathway, and compound detection by inventors Bari et al., filed Jun. 18, 2021 and published Dec. 23, 2021, describes a method applying permutation procedures to mediation and moderation tests of multiple hypotheses, while controlling the rate of false positives. The techniques are shown through a platform-independent tool can be applied to a variety of datasets in diverse and interdisciplinary fields, such as biology and medicine, where integration of multi-scale data is utilized to unmask disease diagnosis, prognosis, susceptibility/resilience, treatment optimization, and biopharmaceutical development for any brain-based, psychological, or medical illness. This platform allows for study of human illness where animal models are proving inadequate.

US Patent Publication No. 2020/0357520 for Diagnosis support apparatus by inventors Fujimoto et al., filed May 8, 2020 and published Nov. 12, 2020, describes a diagnosis support apparatus according to an embodiment including a memory and processing circuitry. The memory stores therein a plurality of types of living body information including gene expression and mutation information, epigenetic environment influence information, protein expression information, signal transmission information, immune function information, endocrine function information, pathological information, image diagnosis information, physiological information, and body findings and symptom information of a subject. The processing circuitry determines a living body state of the subject on the basis of a plurality of analysis results obtained by analysis of the types of living body information.

SUMMARY OF THE INVENTION

The present invention relates to a telemedicine platform, and more specifically to telemedicine platforms including virtual physicians It is an object of this invention to provide a telemedicine platform having a virtual practitioner for interfacing with patients.

In one embodiment, the present invention is directed to a telemedicine system, including at least one server, including a processor and a memory, and at least one database, wherein the at least one server is in network communication with at least one patient user device, wherein the at least one server includes an artificial intelligence module, wherein the artificial intelligence module receives messages from the at least one patient user device and automatically detects described symptoms and/or provides a list of suggested healthcare providers to the at least one patient user device based on natural language processing of the messages, wherein the artificial intelligence module automatically generates responses to the messages from the at least one patient user device to prompt for further information, and wherein the artificial intelligence module generates an animated human face and animates the animated human face to synchronize lip movements to audio of the automatically generated responses.

In another embodiment, the present invention is directed to a telemedicine system, including at least one server, including a processor and a memory, and at least one database, wherein the at least one server is in network communication with at least one patient user device, wherein the at least one server includes an artificial intelligence module, wherein the artificial intelligence module receives messages from the at least one patient user device and automatically detects described symptoms and/or provides a list of suggested healthcare providers to the at least one patient user device based on natural language processing of the messages, wherein the artificial intelligence module automatically generates responses to the messages from the at least one patient user device to prompt for further information, wherein the artificial intelligence module generates audio of the automatically generated responses and transmits the audio to the at least one patient user device, and wherein the list of suggested healthcare providers is based on a geolocation of the at least one patient user device, consultation prices for different healthcare providers, estimated time until an available consultation, and/or average ratings of healthcare providers.

In yet another embodiment, the present invention is directed to a telemedicine system, including at least one server, including a processor and a memory, and at least one database, wherein the at least one server is in network communication with at least one patient user device and at least one practitioner device, wherein the at least one server receives a selection of available consultation times from the at least one practitioner device, wherein the at least one server automatically updates the selection of available consultation times when appointments are made, wherein the at least one server includes an artificial intelligence module, wherein the artificial intelligence module receives messages from the at least one patient user device and automatically detects described symptoms and/or provides a list of suggested healthcare providers to the at least one patient user device based on natural language processing of the messages, wherein the artificial intelligence module automatically generates responses to the messages from the at least one patient user device to prompt for further information, and wherein the artificial intelligence module generates audio of the automatically generated responses and transmits the audio to the at least one patient user device.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 3 illustrates an appointment schedule page for a practitioner GUI according to one embodiment of the present invention.

FIG. 4 illustrates a profile management page for a practitioner GUI according to one embodiment of the present invention.

FIG. 8 illustrates a calendar page for a practitioner GUI according to one embodiment of the present invention.

FIG. 10 illustrates a patient details page for a practitioner GUI according to one embodiment of the present invention.

Figure 11A:
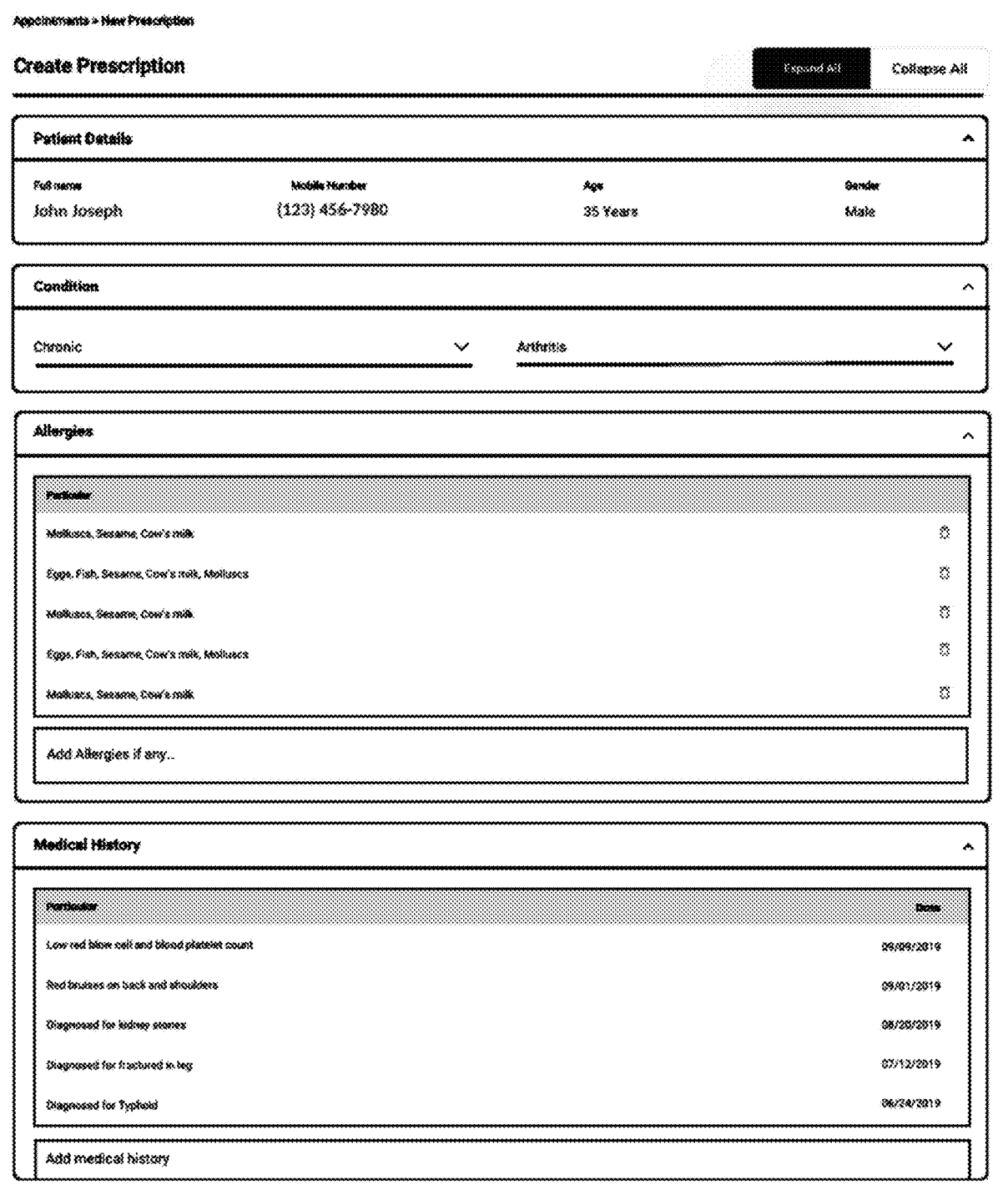
Figure 11B:
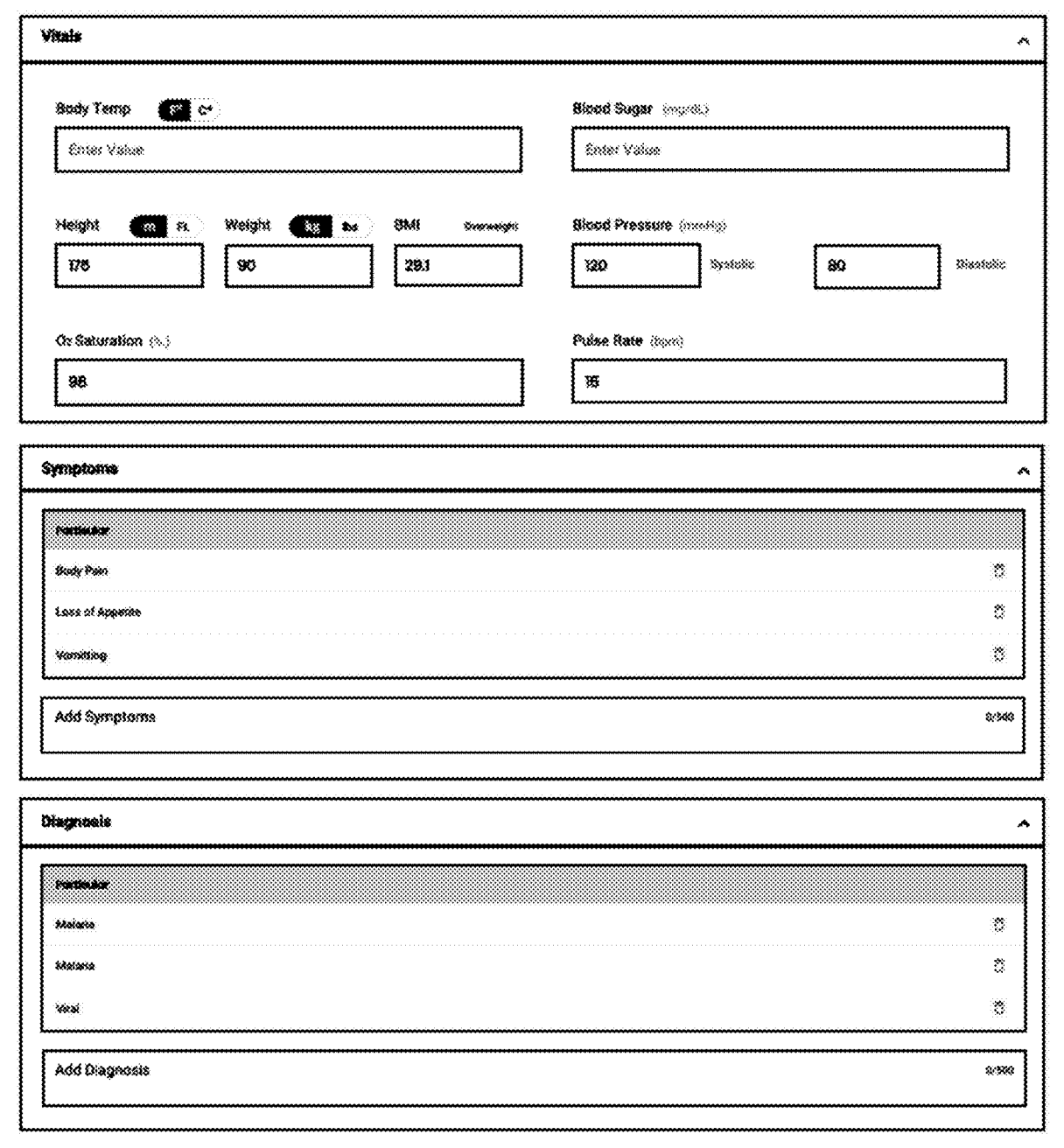
Figure 11C:
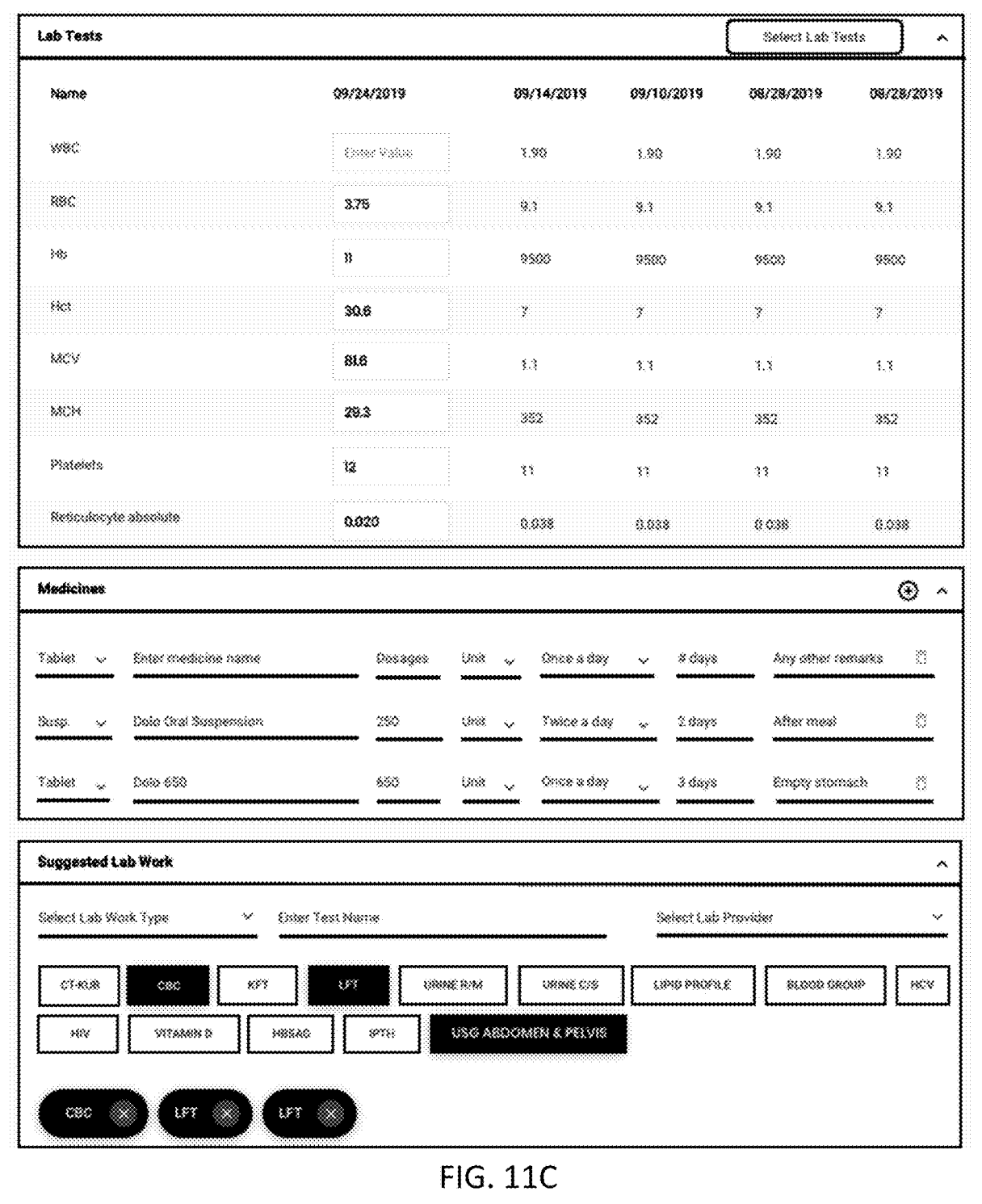
Figure 11D:
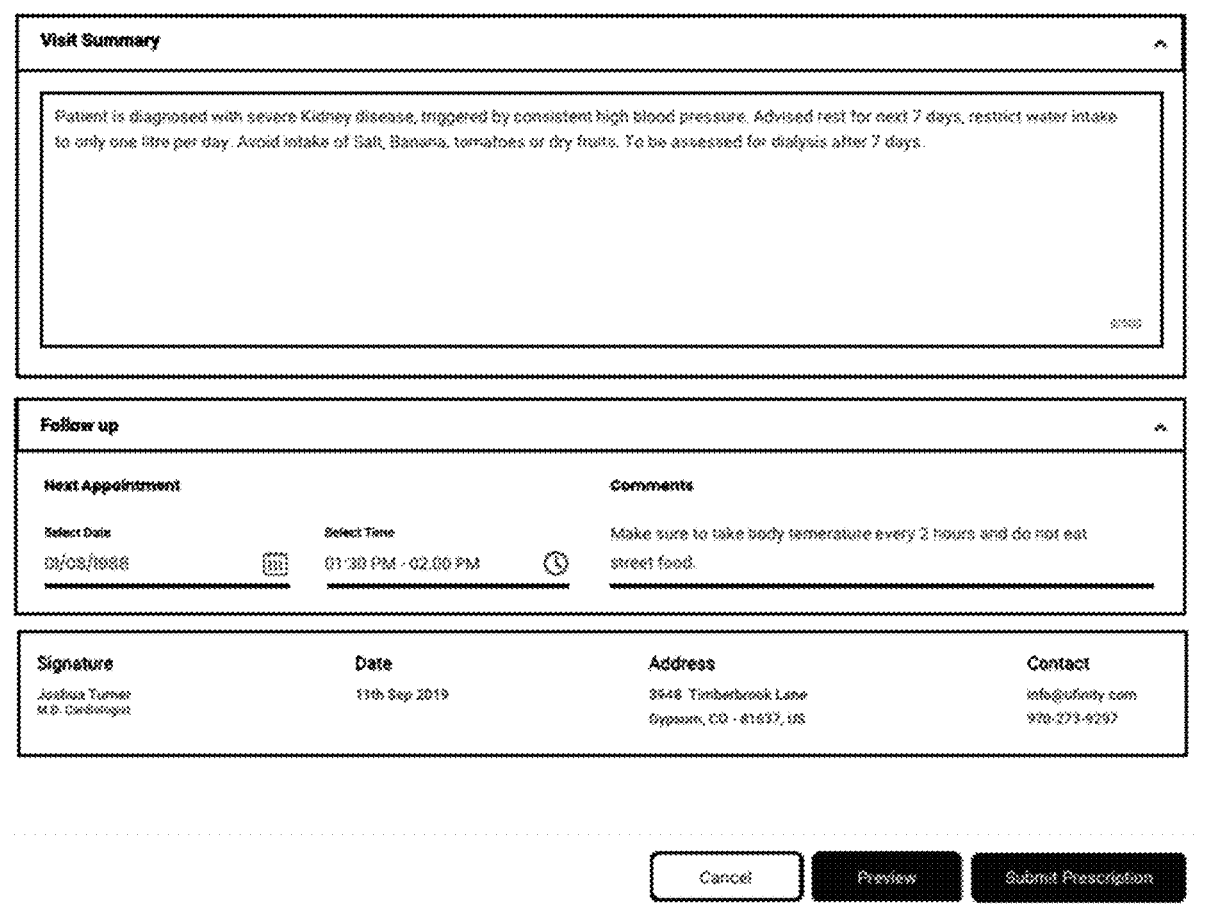

FIG. 11A illustrates a prescription creation page for a practitioner GUI according to one embodiment of the present invention.

FIG. 11B is a continuation of the prescription creation page of FIG. 11A.

FIG. 11C is a continuation of the prescription creation page of FIGS. 11A and 11B.

FIG. 11D is a continuation of the prescription creation page of FIGS. 11A-C.

FIG. 13 is a practitioner management page for an administrator GUI according to one embodiment of the present invention.

FIG. 14 is an account verification management page for an administrator GUI according to one embodiment of the present invention.

FIG. 16 is a patient management page for an administrator GUI according to one embodiment of the present invention.

DETAILED DESCRIPTION

Figure 1A:
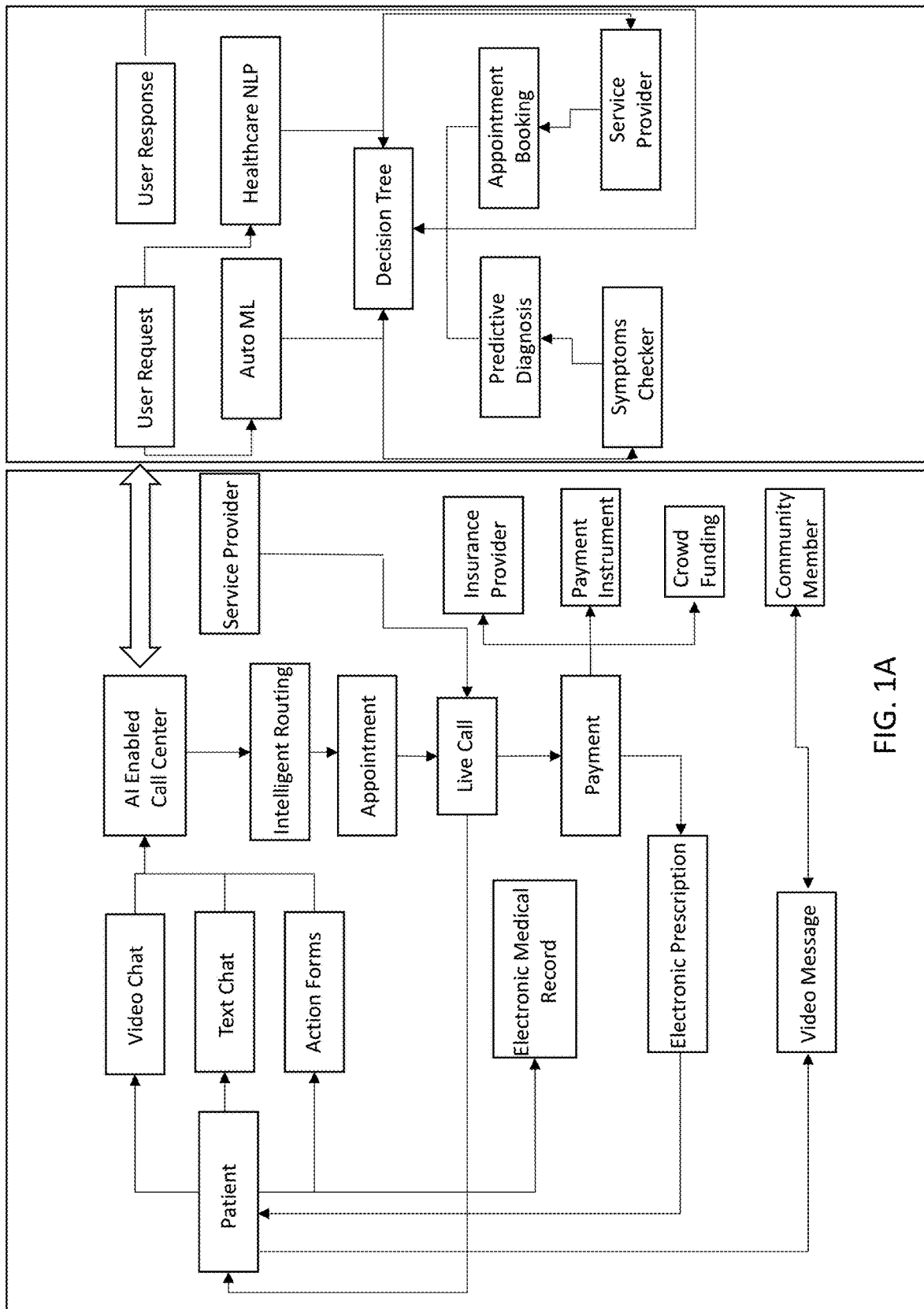
FIG. 1A illustrates a schematic diagram of a system of the present invention.

The present invention is generally directed to a telemedicine platform, and more specifically to telemedicine platforms including virtual physicians In one embodiment, the present invention is directed to a telemedicine system, including at least one server, including a processor and a memory, and at least one database, wherein the at least one server is in network communication with at least one patient user device, wherein the at least one server includes an artificial intelligence module, wherein the artificial intelligence module receives messages from the at least one patient user device and automatically detects described symptoms and/or provides a list of suggested healthcare providers to the at least one patient user device based on natural language processing of the messages, wherein the artificial intelligence module automatically generates responses to the messages from the at least one patient user device to prompt for further information, and wherein the artificial intelligence module generates an animated human face and animates the animated human face to synchronize lip movements to audio of the automatically generated responses.

In another embodiment, the present invention is directed to a telemedicine system, including at least one server, including a processor and a memory, and at least one database, wherein the at least one server is in network communication with at least one patient user device, wherein the at least one server includes an artificial intelligence module, wherein the artificial intelligence module receives messages from the at least one patient user device and automatically detects described symptoms and/or provides a list of suggested healthcare providers to the at least one patient user device based on natural language processing of the messages, wherein the artificial intelligence module automatically generates responses to the messages from the at least one patient user device to prompt for further information, wherein the artificial intelligence module generates audio of the automatically generated responses and transmits the audio to the at least one patient user device, and wherein the list of suggested healthcare providers is based on a geolocation of the at least one patient user device, consultation prices for different healthcare providers, estimated time until an available consultation, and/or average ratings of healthcare providers.

In yet another embodiment, the present invention is directed to a telemedicine system, including at least one server, including a processor and a memory, and at least one database, wherein the at least one server is in network communication with at least one patient user device and at least one practitioner device, wherein the at least one server receives a selection of available consultation times from the at least one practitioner device, wherein the at least one server automatically updates the selection of available consultation times when appointments are made, wherein the at least one server includes an artificial intelligence module, wherein the artificial intelligence module receives messages from the at least one patient user device and automatically detects described symptoms and/or provides a list of suggested healthcare providers to the at least one patient user device based on natural language processing of the messages, wherein the artificial intelligence module automatically generates responses to the messages from the at least one patient user device to prompt for further information, and wherein the artificial intelligence module generates audio of the automatically generated responses and transmits the audio to the at least one patient user device.

Telemedicine platforms are considered an important improvement to medicine, especially to provide care for patients too far to reasonably travel to a physician, patients who are in poor physical condition and unable to easily travel, or patients whose local hospital is overly crowded. It is particularly useful for allowing physicians in highly populated states or areas to serve patients in less populated areas or states. Furthermore, telemedicine is an effective way to reduce time investment by both patients and physicians, increasing convenience in an increasingly busy society. Telemedicine is also likely to reduce overall expenses for patients. From a public policy perspective, telemedicine helps to conserve supplies and bed space that otherwise is able to go to patients unable to be treated remotely.

Beginning in 2020, the COVID-19 pandemic has greatly increased interest in telemedicine, as on-location visitations became much more limited. Some polls have shown signs that telemedicine and telehealth options will continue to be very popular even with the pandemic subsiding. For example, one poll from Doctor.com showed that 83% of patients expected to use telehealth and telemedicine options even after the COVID-19 pandemic ended. Furthermore, a 2019 Harris Poll showed that about two thirds of patients were open to trying telehealth options even before the pandemic started, despite only a small percentage having used any telehealth platforms.

With telemedicine, it is no longer necessary for patients to spend long times in waiting rooms. Moreover, in some situations, particularly hospitals that are nearby a patient are particularly busy and/or understaffed. In the traditional medical system, this leads to patients spending larger amounts of time in the hospital, increasing stress levels and decreasing satisfaction levels. Alternatively, many patients choose to leave rather than wait, creating missed opportunities for patient health. Telemedicine allows the patients to access clinical advice across longer distances, facilitating more consistent access to healthcare professionals for individuals regardless of geographical area.

Referring now to the drawings in general, the illustrations are for the purpose of describing one or more preferred embodiments of the invention and are not intended to limit the invention thereto.

FIG. 1A illustrates a schematic diagram of a system of the present invention. In one embodiment, the platform receives a selection to engage in video chat, text chat, and/or the platform receives an action form from a user device associated with a patient profile. The request for video chat and/or text chat is automatically routed to an artificial intelligence (AI)-enabled call center. The AI-enabled call center processes user requests with natural language processing (NLP) specifically adapted to healthcare needs. The AI-enabled call center then uses a decision tree supported by automated machine learning (ML) to process the request. In one embodiment, processing the request includes determining a desired plan of action (e.g., speaking to a live physician) and/or determining a list of symptoms described by the patient. In one embodiment, the decision tree is used to determine a predictive diagnosis for the patient based on the described symptoms and match the patient with a physician and/or provide other medical advice based on the diagnosis. In one embodiment, the AI-enabled call center automatically prompts for additional information to support the decision tree. If the AI-enabled call center determines that a call with a live physician is desired, then the AI-enabled call center prompts the user to determine a suitable appointment time based on the availability of relevant physicians. In one embodiment, the live physician The platform is then able to facilitate a live call (e.g., audio call, video call, etc.) between a service provider and the patient. The platform is then able to automatically facilitate consultation billing for the call, including facilitating insurance payments. If the service provider has prescribed anything to the patient, the platform is then able to automatically inform a relevant pharmacy of the prescription and notify the patient regarding details of the prescription. Furthermore, the platform is able to automatically generate and/or update an electronic medical record of the patient based on the results of each consultation.

In one embodiment, the platform automatically tracks the amount of time spent by each doctor on the platform in consultations. In this way, the platform is able to facilitate use of the platform as going toward residency hours for physicians, offering incentives for use of the platform beyond monetary reward.

The present invention provides a telemedicine program, including at least one server, itself including a processor and a memory, and at least one database. The platform is operable to receive a selection from at least one user device (e.g., a smart phone, a tablet, a computer, a smart watch, etc.) to generate at least one patient profile and is operable to store a multiplicity of patient profiles. Each patient profile includes a username, a password, at least one profile picture, at least one email address, at least one phone number, demographic data (e.g., age, ethnicity, gender, etc.), at least one home address, at least one designated pharmacy for receiving prescriptions, previous test data, and/or other information. The platform is further operable to receive a selection from at least one practitioner device (e.g., a smart phone, a tablet, a computer, a smart watch, etc.) to generate at least one practitioner profile and is operable to store a multiplicity of practitioner profiles. Each practitioner profile includes a username, a password, at least one profile picture, at least one email address, at least one phone number, at least one pager number, a schedule of upcoming appointments, meetings, and obligations, patient data for patients seen by the practitioner, and/or other information.

The telemedicine platform is able to match patient accounts with at least one physician based on patient preference information, patient symptoms, geographical information, language preferences, and/or other information. The telemedicine platform also includes at least one artificial intelligence module operable to automatically diagnose a patient based on at least one description of symptoms, patient demographic data, at least one image, at least one video, at least one test result (including, but not limited to, electroencephalogram (EEG) data, electrocardiogram (EKG) data, etc.), and/or at least one scan (e.g., a computerized tomography (CT) scan, a magnetic resonance imaging (MRI) scan, an X-ray scan, etc.).

In one embodiment, the telemedicine platform includes an integrated billing module. After a consultation or session, the integrated billing module is operable to display an amount of money due by the patient. In one embodiment, the integrated billing module is operable to display a line-item breakdown of expenses associated with a patient profile. In one embodiment, the integrated billing module is operable to display costs associated with a patient profile before and after insurance, allowing for improved transparency. The integrated billing module receives information corresponding to at least one financial account and/or at least one associated insurance plan from a user device associated with a patient. In one embodiment, the information corresponding to the at least one financial account includes checking account information, credit card information, wire transfer information, information corresponding to at least one cryptocurrency wallet, and/or information corresponding to any other type of financial account or profile. The platform then automatically sends a request to at least one financial entity associated with the financial account or profile (i.e., a bank, a credit card provider, etc.). The platform is then capable of automatically settling the bill.

Figure 1B:
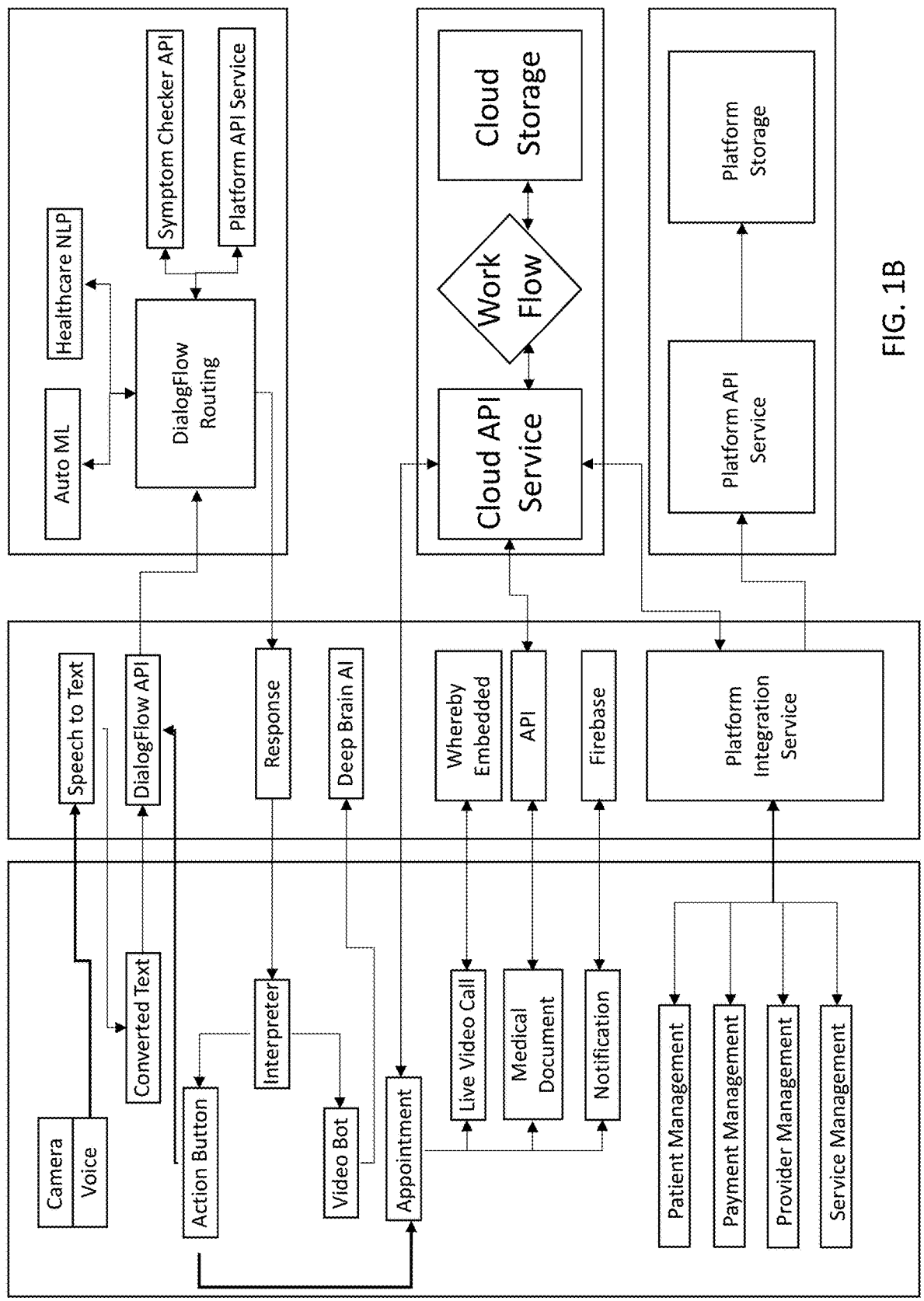
FIG. 1B illustrates a schematic diagram of a system of the present invention.

FIG. 1B illustrates a schematic diagram of a system of the present invention. In one embodiment, the platform receives at least one image and/or at least one voice message from a user device. The system automatically translates the at least one voice message and/or at least one image (e.g., text image) to a text string and feeds the text string through a dialogue application programming interface (API) to a machine learning-based dialogue analysis module. In another embodiment, the system receives a text string directly form the user device. The machine learning-based dialogue analysis module automatically uses natural language processing (NLP) to analyze the text and accesses a symptom checker API (e.g., Infermedica, GOOGLE HEALTH CLOUD) in order to automatically generate a list of likely symptoms based on the text. In one embodiment, the list of likely symptoms is generated as International Classification of Diseases (ICD)-10 diagnosis codes.

Based on the analysis of the received text, the machine learning-based dialogue analysis module automatically generates a response and transmits the response to the user device. In one embodiment, the generated response is delivered by at least one AI-based virtual assistant. In one embodiment, the AI-based virtual assistant is generated by at least one external API (e.g., DEEP BRAIN AI). In one embodiment, based on the text analysis, the machine learning-based dialogue analysis module automatically prompts for additional information. In one embodiment, based on the text analysis, the machine learning-based dialogue analysis module automatically transmits a prompt to schedule an appointment for a human doctor consultation (e.g., via video call). In one embodiment, the list of likely symptoms is automatically transmitted to the human doctor chosen by the user device. In one embodiment, the chosen doctor and the list of likely symptoms are automatically saved on a cloud server. This information is readily retrievable by any doctor operating on the platform and working with the patient for purposes of patient management, payment management, provider management, and service management.

Figure 2:
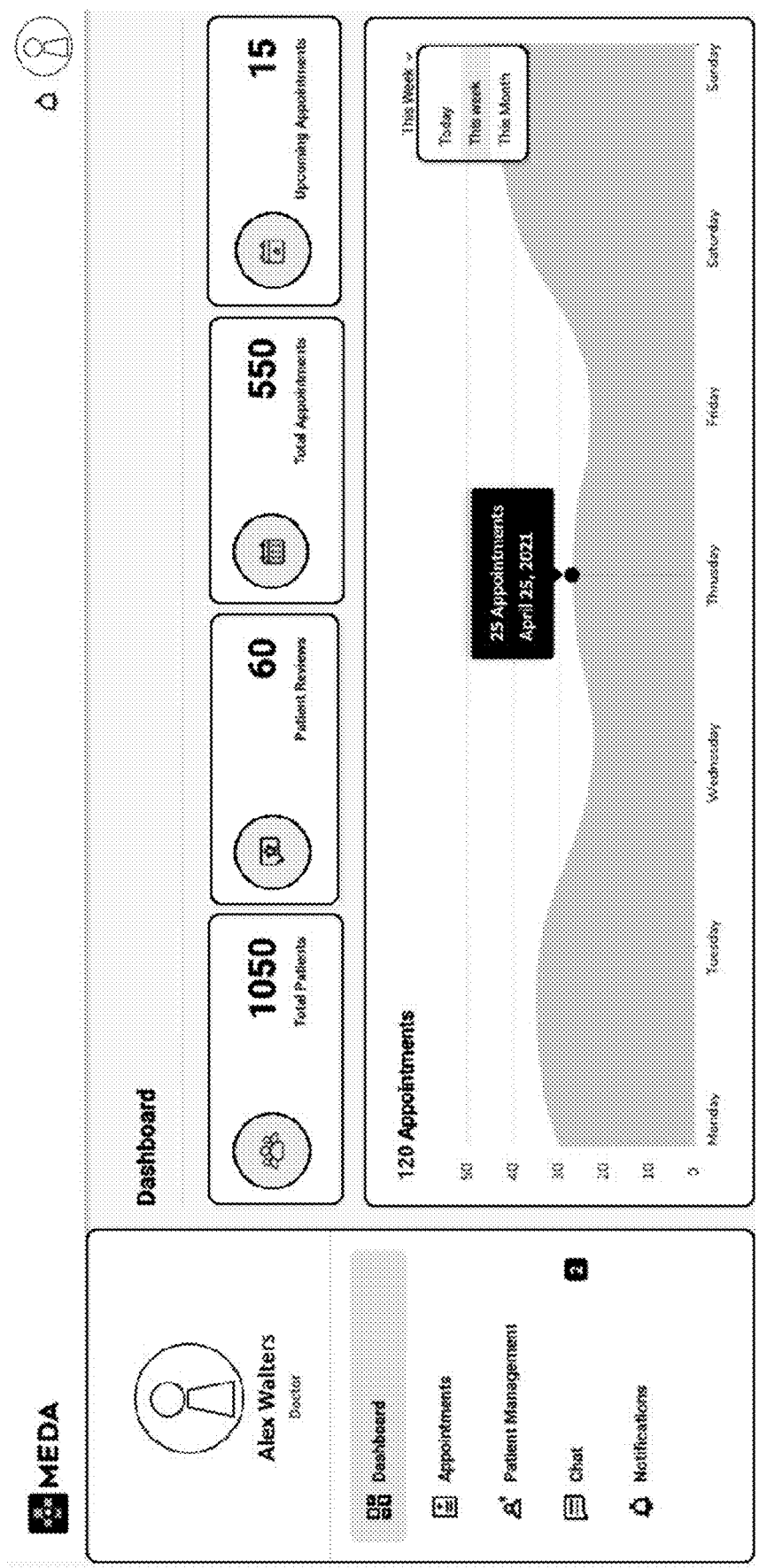
FIG. 2 illustrates a home dashboard page for a practitioner graphical user interface (GUI) according to one embodiment of the present invention.

FIG. 2 illustrates a home dashboard page for a practitioner graphical user interface (GUI) according to one embodiment of the present invention. In one embodiment, the platform includes at least three separate interfaces: a practitioner interface, an administrative interface, and a patient interface. The practitioner interface is able to be accessed by logging into a practitioner profile. The practitioner interface includes a dashboard including a list of upcoming appointments, a number of total patients for the practitioner, a number of total patient reviewers for the practitioner, a total number of appointments (including prior appointments), a total number of upcoming appointments, a number of appointments for the current day (or current week, month, year, etc.) a list of patient test results, an inbox including notification for chat messages from and/or other alerts from one or more patients. As shown in FIG. 2, in one embodiment, the dashboard page includes a graphical representation of number of appointments per day (or per week, per month, etc.) over a preset timespan (e.g., this week, this month, this year, etc.).

FIG. 3 illustrates an appointment schedule page for a practitioner GUI according to one embodiment of the present invention. In one embodiment, the appointment schedule page includes a list of patients who have upcoming appointments, a gender of each patient, a time for each appointment, a date for each appointment, a contact means for each patient (e.g., phone number, email address, etc.), a status of each appointment (e.g., past, upcoming, pending, etc.). In one embodiment, through the appointment schedule page, the platform receives selections to create prescriptions associated with one or more of the appointments, edit upcoming appointments, and/or cancel appointments.

In one embodiment, the list of upcoming appointments is organized on a calendar interface. Through the practitioner interface, the platform receives selections by at least one practitioner device to cancel appointments and/or choose new times for an appointment. Furthermore, through the practitioner interface, at least one practitioner device is able to receive a request for audio and/or video communication for virtual consultations.

FIG. 4 illustrates a profile management page for a practitioner GUI according to one embodiment of the present invention. Through the profile management page, the platform is operable to receive an input to add, delete, and/or edit information such as a first name, a last name, a middle name, a gender, one or more proficient languages, one or more phone numbers, one or more designations (e.g., doctor, nurse, administrator, surgeon, etc.), an amount of experience (e.g., a number of years of experience), a date of birth, one or more email addresses, a unique identifier (e.g., a registration number), one or more specializations, one or more practice areas, one or more qualifications, one or more departments), brief description about one's self and/or one's practice, at least one profile picture, and/or other personal identifying information.

Figure 5:
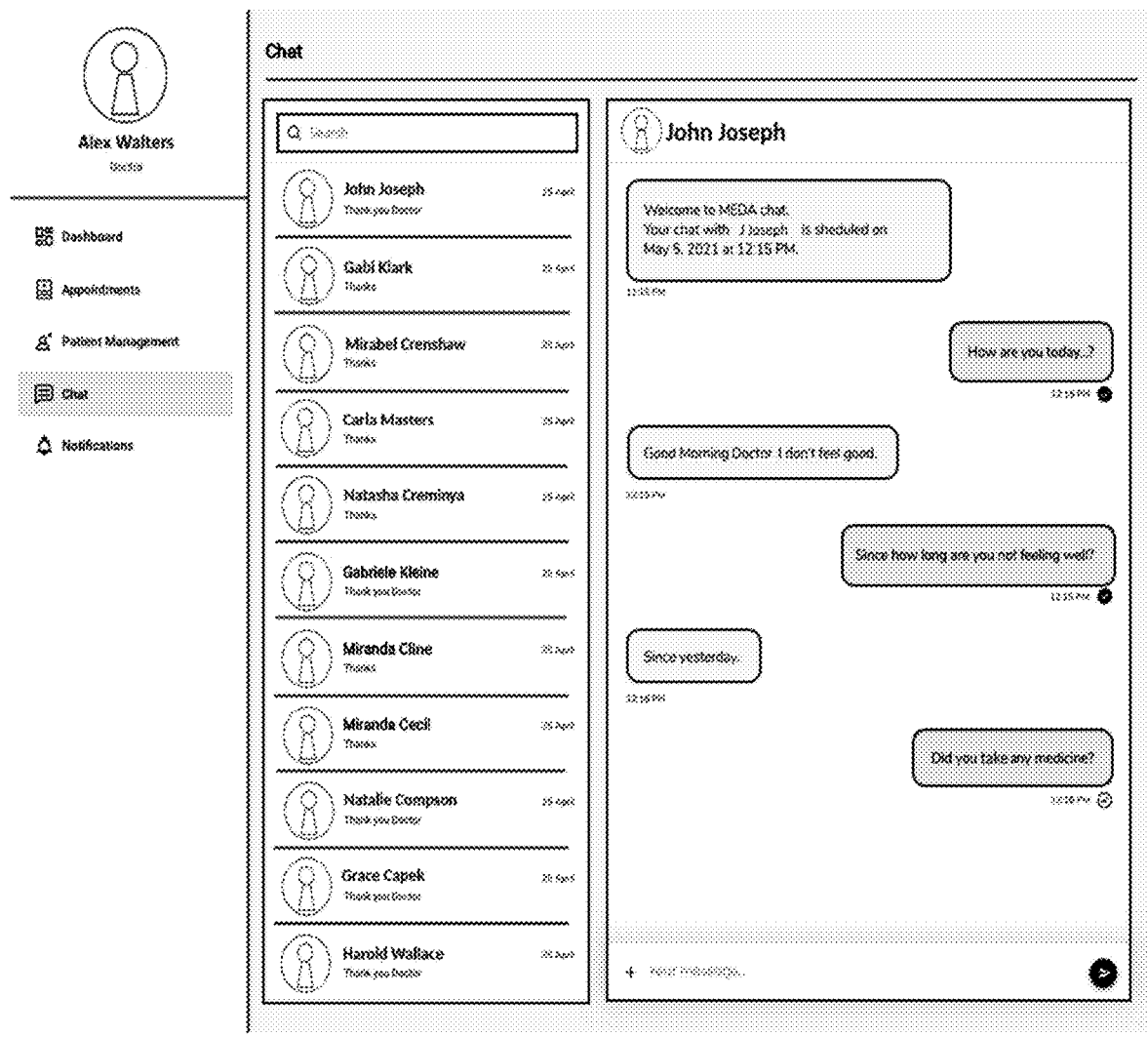
FIG. 5 illustrates a text chat page for a practitioner GUI according to one embodiment of the present invention.

FIG. 5 illustrates a text chat page for a practitioner GUI according to one embodiment of the present invention. In one embodiment, the practitioner interface includes a text chat page for sending messages to and/or receiving messages from patients. In one embodiment, the text chat page includes search functionality to search for conversations with specific patients.

Figure 6:
FIG. 6 illustrates a scheduling management page for a practitioner GUI according to one embodiment of the present invention.

FIG. 6 illustrates a scheduling management page for a practitioner GUI according to one embodiment of the present invention. In one embodiment, through a scheduling management page, the platform is able to receive designations of when a physician is free to meet with patients. In one embodiment, the scheduling management includes a plurality of sliders for each day of the week (or month, or year, etc.) wherein areas covered by the sliders are available and areas not covered by the sliders are not available. In another embodiment, days are divided into discrete intervals (e.g., 15 min, 30 min, 1 hour, 2 hours, etc.) and the platform is operable to receive a designation of one or more of the discretized time slots when the practitioner is available. In one embodiment, when a patient sets an appointment with the practitioner, the platform automatically removes the set time slot from the available times on the schedule. Setting available times is particularly important, as it allows the system to more accurately match patients with practitioners based on when each practitioner is available. In one embodiment, the scheduling management page is also able to receive a selection of a consultation fee, a starting working hour, and/or a final working hour. In one embodiment, the scheduling management page displays one or more reviews written by patients with regard to the practitioner.

Figure 7:
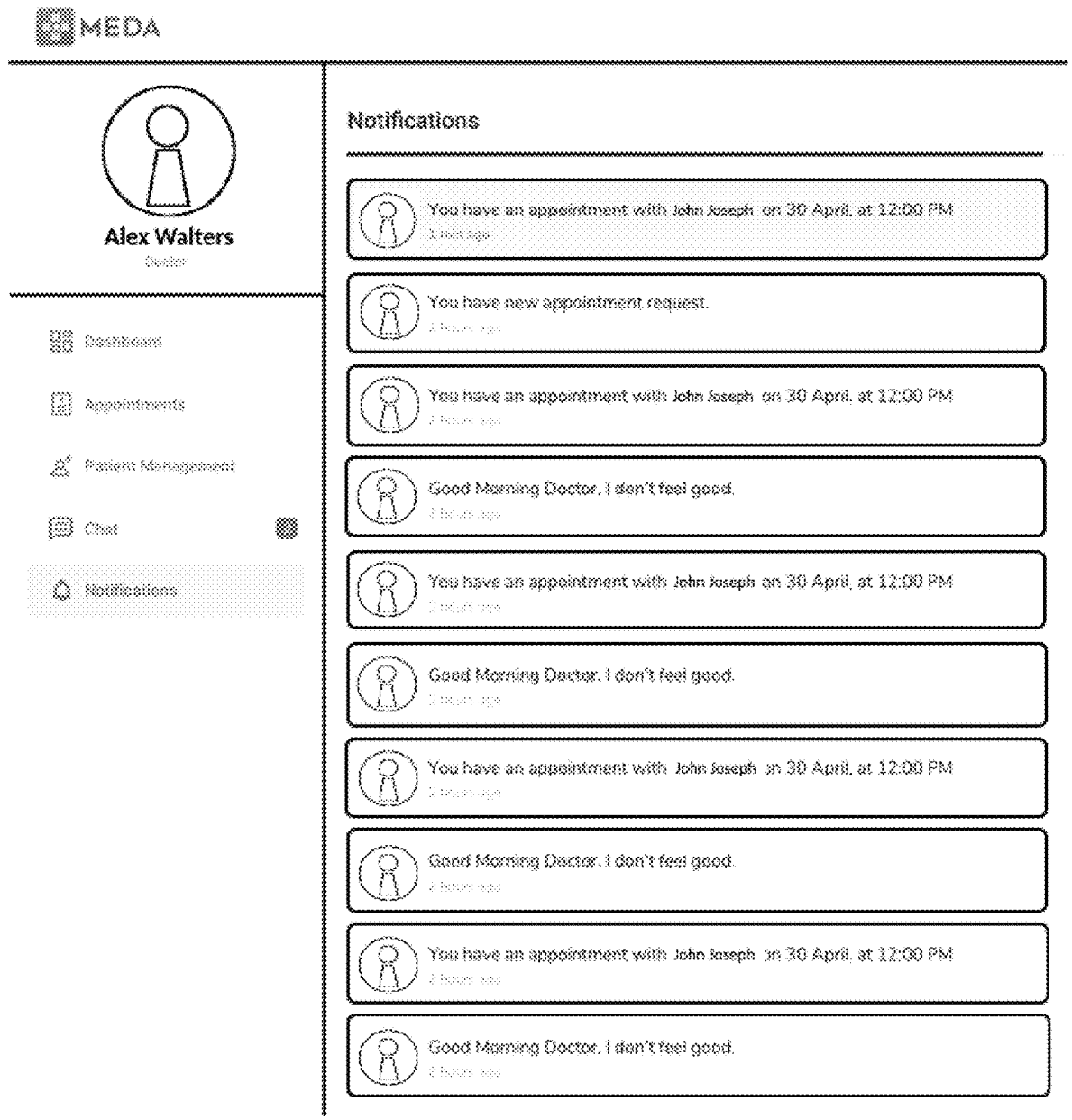
FIG. 7 illustrates a notification page for a practitioner GI according to one embodiment of the present invention.

FIG. 7 illustrates a notification page for a practitioner GI according to one embodiment of the present invention. The notification page provides a list of notifications regarding, by way of example and not limitation, upcoming appointments, patient alerts, available test data, upcoming internal meetings, and/or other alert times custom-created by the practitioner.

Figure 8:
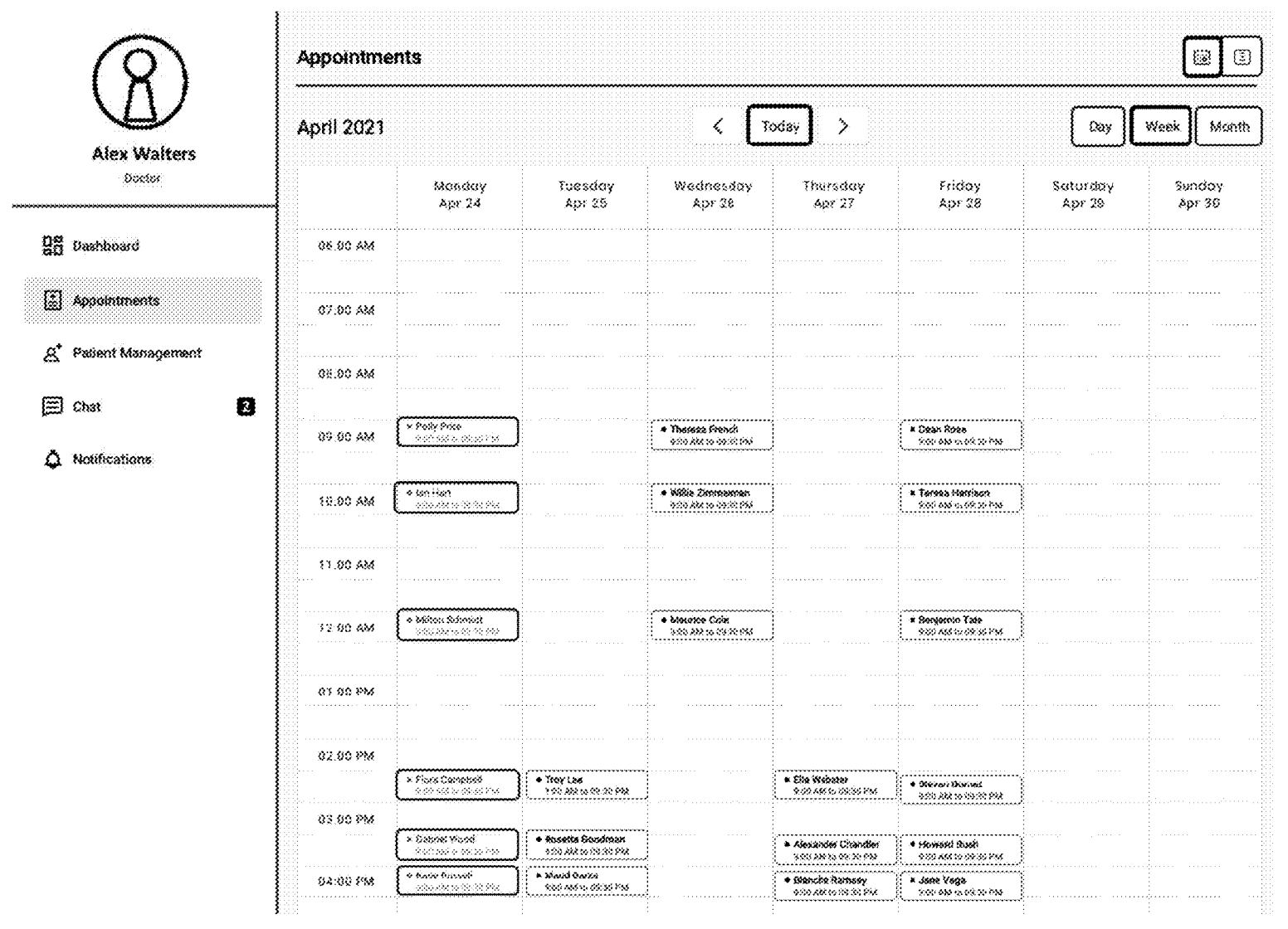

FIG. 8 illustrates a calendar page for a practitioner GUI according to one embodiment of the present invention. In one embodiment, the practitioner GUI includes a calendar page. The calendar page provides an hour-by-hour listing of appointments and/or other meetings for the practitioner for one or more days (e.g., a week, two weeks, a month, etc.). By organizing the meetings onto a calendar interface, practitioners are better able to visualize upcoming events and plan accordingly.

Figure 9:
FIG. 9 illustrates a patient management page for a practitioner GUI according to one embodiment of the present invention.

FIG. 9 illustrates a patient management page for a practitioner GUI according to one embodiment of the present invention. In one embodiment, the practitioner interface includes a patient list, whereby the practitioner is able to view a list of all patients currently seeing the practitioner (or who currently have scheduled appointments). In one embodiment, the patient list includes a patient identification sequence, a name, an email address, a phone number, and/or a status of the patient (e.g., appointment completed, pending appointment, unscheduled appointment, upcoming appointment, etc.) for each patient. In one embodiment, through the patient management page, the practitioner GUI is able to receive a request to deactivate one or more patients, removing those patients from association with the practitioner, often due to death of the patient or transfer of the patient to another practitioner. In one embodiment, the patient management page is operable to receive a request to apply a filter to the list of patients (e.g., view all patients or only pending patients).

Figure 10:
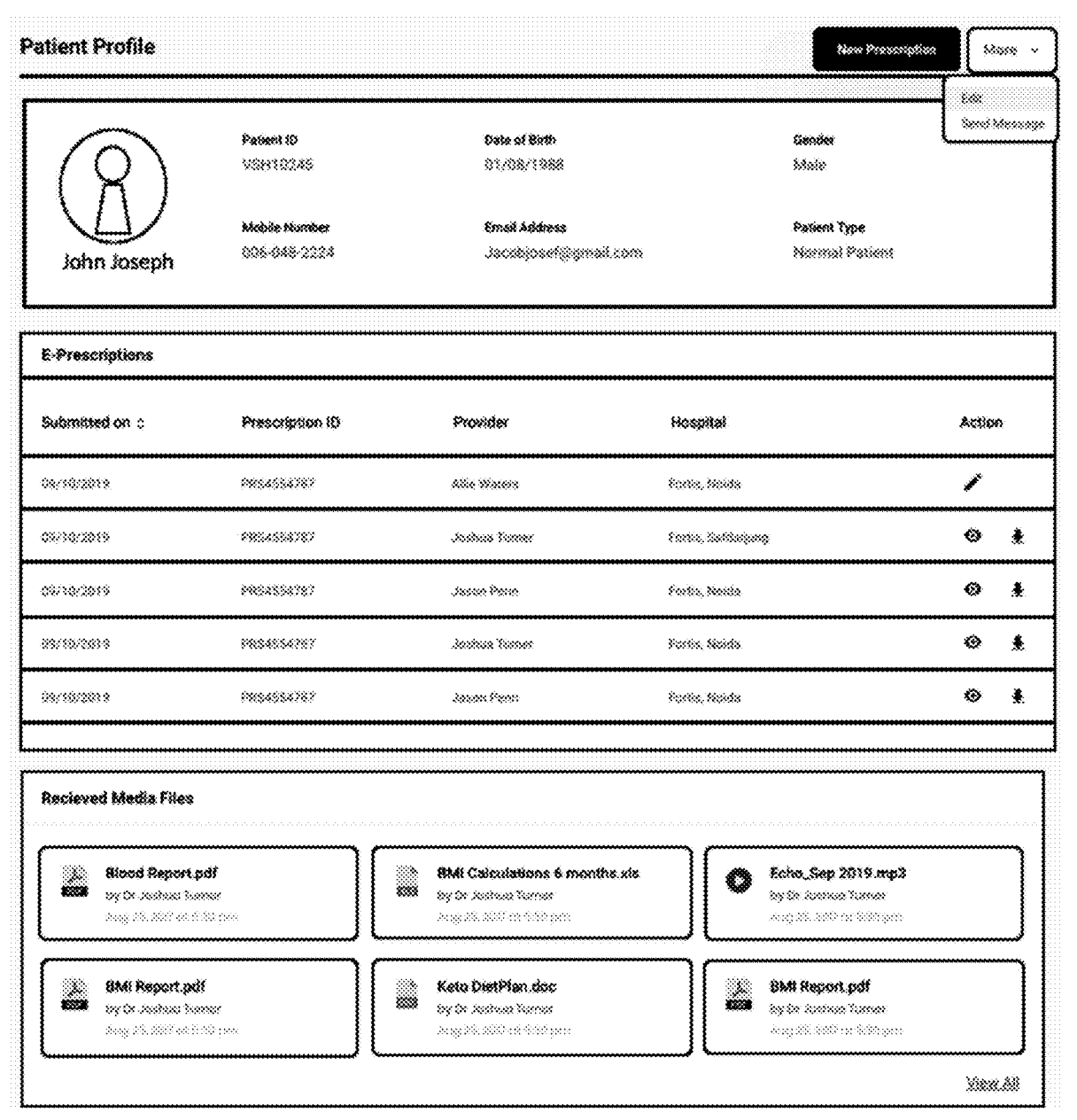

FIG. 10 illustrates a patient details page for a practitioner GUI according to one embodiment of the present invention. In one embodiment, the patient list is able to receive click selection by the practitioner device of one or more patients on the patient list, leading to patient details pages for each of the one or more patients. The patient details page includes personal information regarding each patient, including a name, a profile picture, a patient identification sequence, a date of birth, one or more email addresses, one or more phone numbers, a patient type (e.g., normal patient, emergency patient, minor patient, etc.), and/or a gender. The patient details pages further includes a list of current and/or past prescriptions (including dates when medication was prescribed, hospitals that prescribed each prescription, providers who prescribed each prescription and/or prescription identification numbers), a list of past and future appointments (virtual or in-person) with the patient, demographic information, a list of current symptoms experienced by the patient, and/or other relevant information. In one embodiment, the patient details page further includes a number of attached files (e.g., PDF files, text document files, spreadsheet files, videos, images, etc.) including test results and/or other information for each patient. In one embodiment, through the patient details page, the platform receives requests to edit the patient profile, send a message to the patient, and/or create a new prescription for the patient.

FIGS. 11A-D illustrate a prescription creation page for a practitioner GUI according to one embodiment of the present invention. In one embodiment, through the practitioner interface, the server is able to receive a prescription from a practitioner profile, with the prescription being associated with a patient profile. In one embodiment, in order to generate the prescription, the platform receives personal health information regarding the patient from the practitioner device. In one embodiment, the platform receives information including the name of the patient, at least one contact method for the patient (e.g., a phone number, an email address, a home address, etc.), and/or a gender of the patient. In one embodiment, the platform receives information including any conditions (chronic or otherwise) experienced by the patient, any allergies of the patient, a medical record of the patient (e.g., including past illnesses, surgeries, etc.), vitals information for the patient (e.g., body temperature, blood sugar, height, weight, BMI, blood pressure, $O_2$ saturation and/or pulse rate), current symptoms experienced by the patient, one or more diagnosed conditions for the patient, one or more lab test results, one or more other medicines taken by the patient (prescribed or unprescribed), one or more suggested lab work tests, a text summary of an appointment, a follow-up appointment date and time, additional comments, and/or other health information. In one embodiment, the platform receives a signature from the practitioner device to allow the prescription (e.g., a digital signature, a scanned signed document, etc.). In one embodiment, the platform automatically transmits the prescription information to a designated home pharmacy associated with the patient profile. In one embodiment, the practitioner interface is integrated with at least one third party data management system (e.g., EPIC), including application programming interface (API) plugins providing for automatic transcription with a suggested list of International Classification of Diseases (ICD)-10 diagnosis codes, decreasing the amount of time needed for practitioners to enter and characterize patient symptoms.

Figure 12:
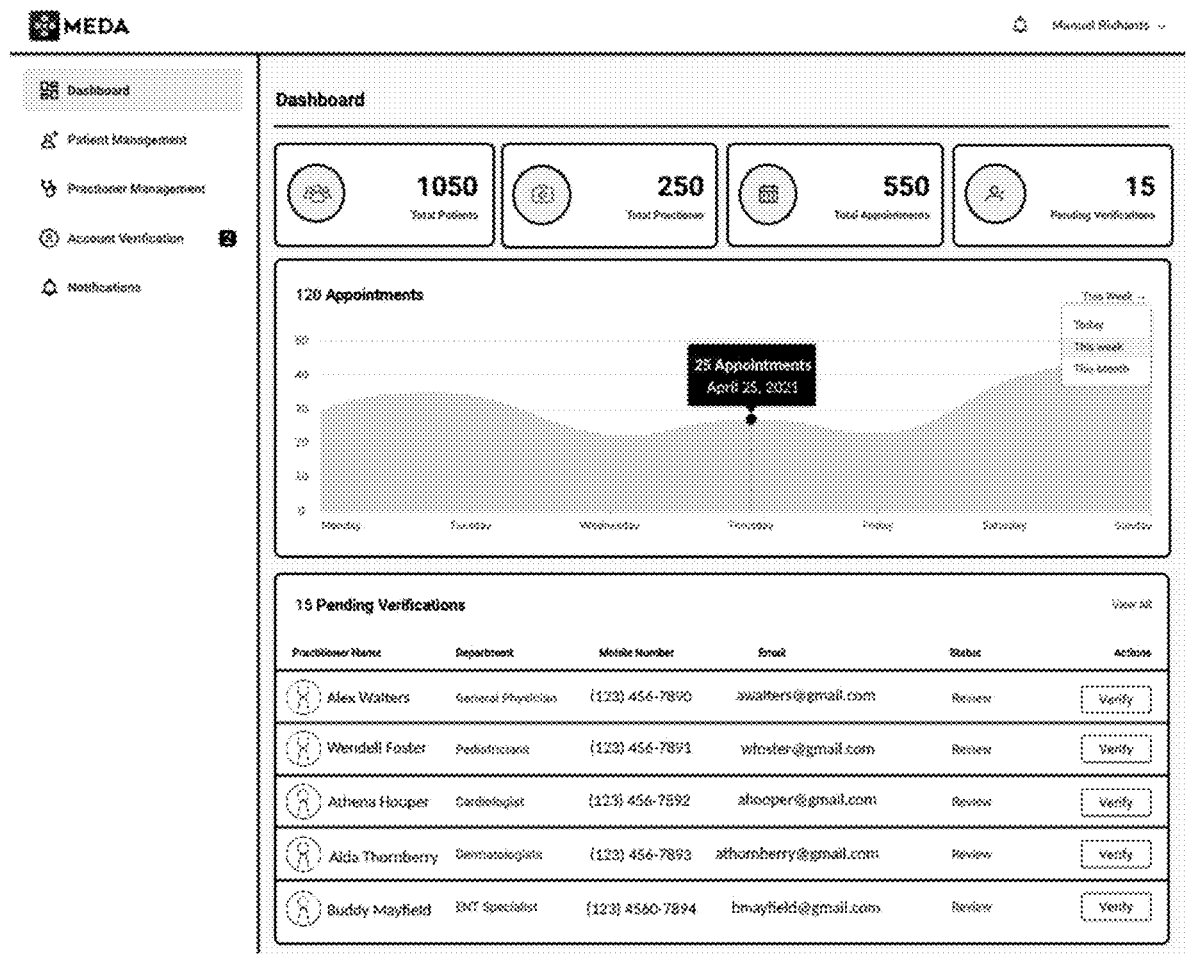
FIG. 12 is a home dashboard page for an administrator GUI according to one embodiment of the present invention.

FIG. 12 is a home dashboard page for an administrator GUI according to one embodiment of the present invention. In one embodiment, the system includes an administrator GUI, operated by, by way of example and not limitation, a hospital administrator or the head of a practice group. The administrator GUI is able to be used for adding and deleting practitioners from a network, and/or managing patients and patient payment. In one embodiment, each practitioner profile on the platform is associated with one or more administrator profile. When a practitioner profile is associated with an administrator profile, the administrator profile is able to access, view, edit, and/or delete information from the practitioner profile. In addition, in one embodiment, when a patient profile is associated with a practitioner profile, the patient profile is also automatically associated with the administrator profile associated with the practitioner profile, allowing the administrator profile to access, view, edit and/or delete information from the patient profile.

In one embodiment, the home dashboard page for the administrator GUI includes a total number of patients associated with the administrator profile, a total number of practitioners associated with the administrator profile, a total number of appointments (past and upcoming) for patients associated with the administrator profile, a number of appointments for patients associated with the administrator profile on the current day, and/or a number of pending verifications for the administrator profile. In one embodiment, as shown in FIG. 12, the dashboard page includes a graphical representation of number of appointments per day (or per week, per month, etc.) over a preset timespan (e.g., this week, this month, this year, etc.). In one embodiment, the dashboard page includes a list of pending verifications, including, by way of example and not limitation, one or more practitioner names, a department for each practitioner, one or more phone numbers for each practitioner, one or more email addresses for each practitioner, and/or a status for each verification (e.g., approved, denied, pending, completed, etc.).

Figure 13:
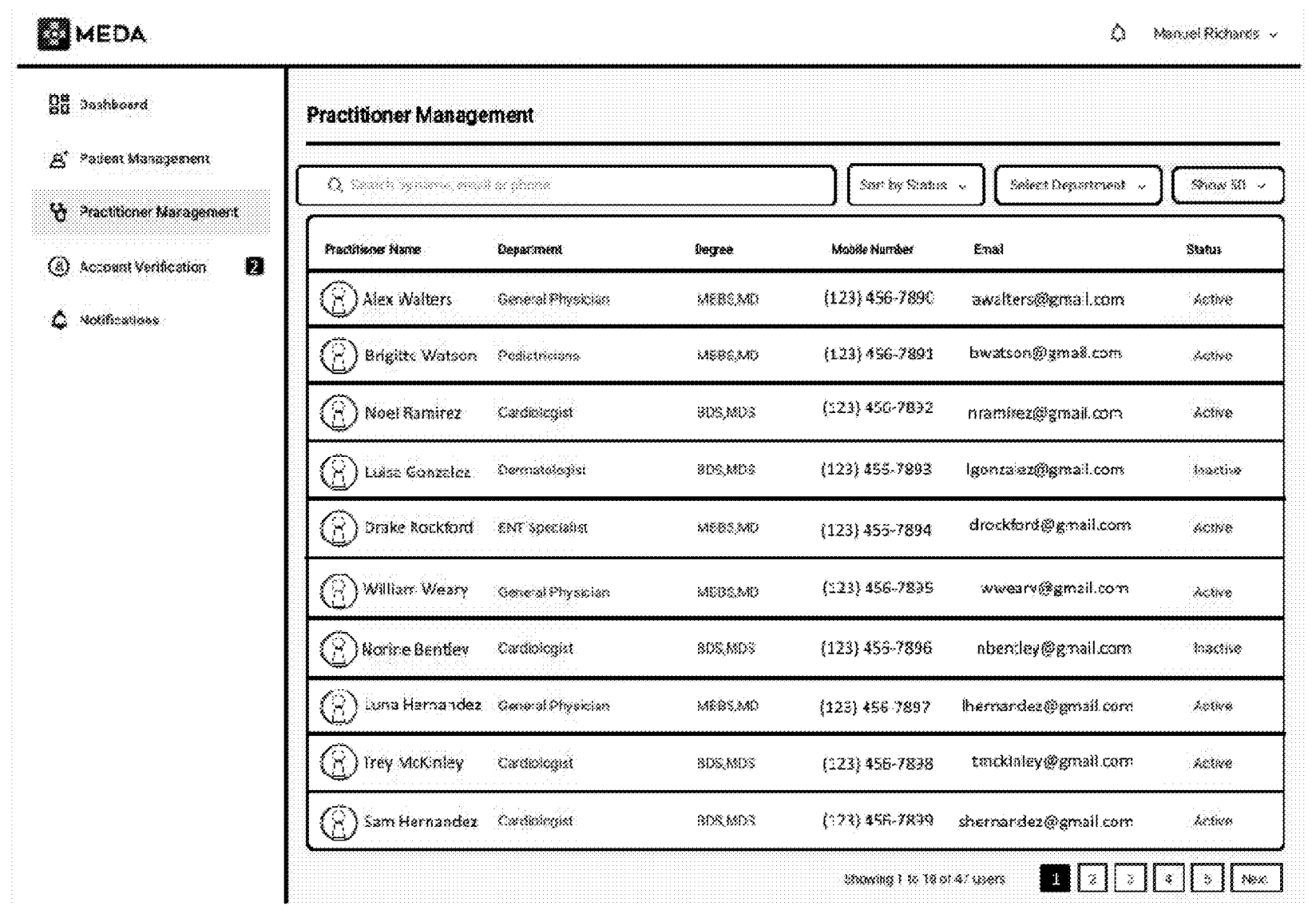

FIG. 13 is a practitioner management page for an administrator GUI according to one embodiment of the present invention. The practitioner management page includes a list of practitioner profiles associated with the administrator profile. In one embodiment, the list includes profile pictures, names, departments, academic degrees, one or more phone numbers, one or more email addresses, and/or a status (active, inactive, etc.) for each practitioner. In one embodiment, the practitioner management page includes search functionality for searching for practitioners based on one or more fields, including name, email and/or phone number. In one embodiment, the platform is able to receive a selection of a filter for the list of practitioners by, by way of example and not limitation, status, department, degree, and/or other fields.

FIG. 14 is an account verification management page for an administrator GUI according to one embodiment of the present invention. The purpose of account verification management is to ensure that individuals have the proper credentials to be brought onto the network, and are who the person claims to be. This is particularly useful for administrators not directly associated with a physical hospital. One method of organization is for administrators to be solely virtual entities, dedicated to associating with specific types of doctors that work for separate hospitals in separate areas. In this situation, it is useful for the administrator to be able to view credentials of any physician before bringing them on board.

The account verification management page for an administrator GUI includes a list of practitioner profiles requesting to be associated with the administrator profile. In one embodiment, the list includes a profile picture, a name, one or more phone numbers, one or more email addresses, a status (e.g., reviewed, pending, rejected, approved, etc.), and/or other information for each practitioner profile on the list. In one embodiment, the account verification management page includes search functionality to search for practitioner profiles based on name, email, phone number, and/or other factors. In one embodiment, the platform receives a selection to filter the list based on status of the verifications and/or other factors. In one embodiment, through the account verification management page, the platform is operable to receive click selection to verify a practitioner profile, automatically generating an individual account verification page for that profile.

Figure 15:
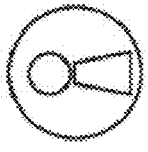
FIG. 15 illustrates an individual account verification page for an administrator GUI according to one embodiment of the present invention.

FIG. 15 illustrates an individual account verification page for an administrator GUI according to one embodiment of the present invention. The individual account verification GUI includes personal information regarding a particular practitioner profile as well as attached documents demonstrating credentials (e.g., references, academic records, certifications, etc.). In one embodiment, the personal information includes a profile picture, a name, a registration number, a consultation fee, normal working hours, amount of experience (e.g., a number of years), a list of degrees, a list of certifications, a practice area, a department, a specialization, at least one email address, at least one number, and/or at least one average rating (i.e., an average rating given by patients associated with or previously associated with the practitioner profile).

Figure 16:
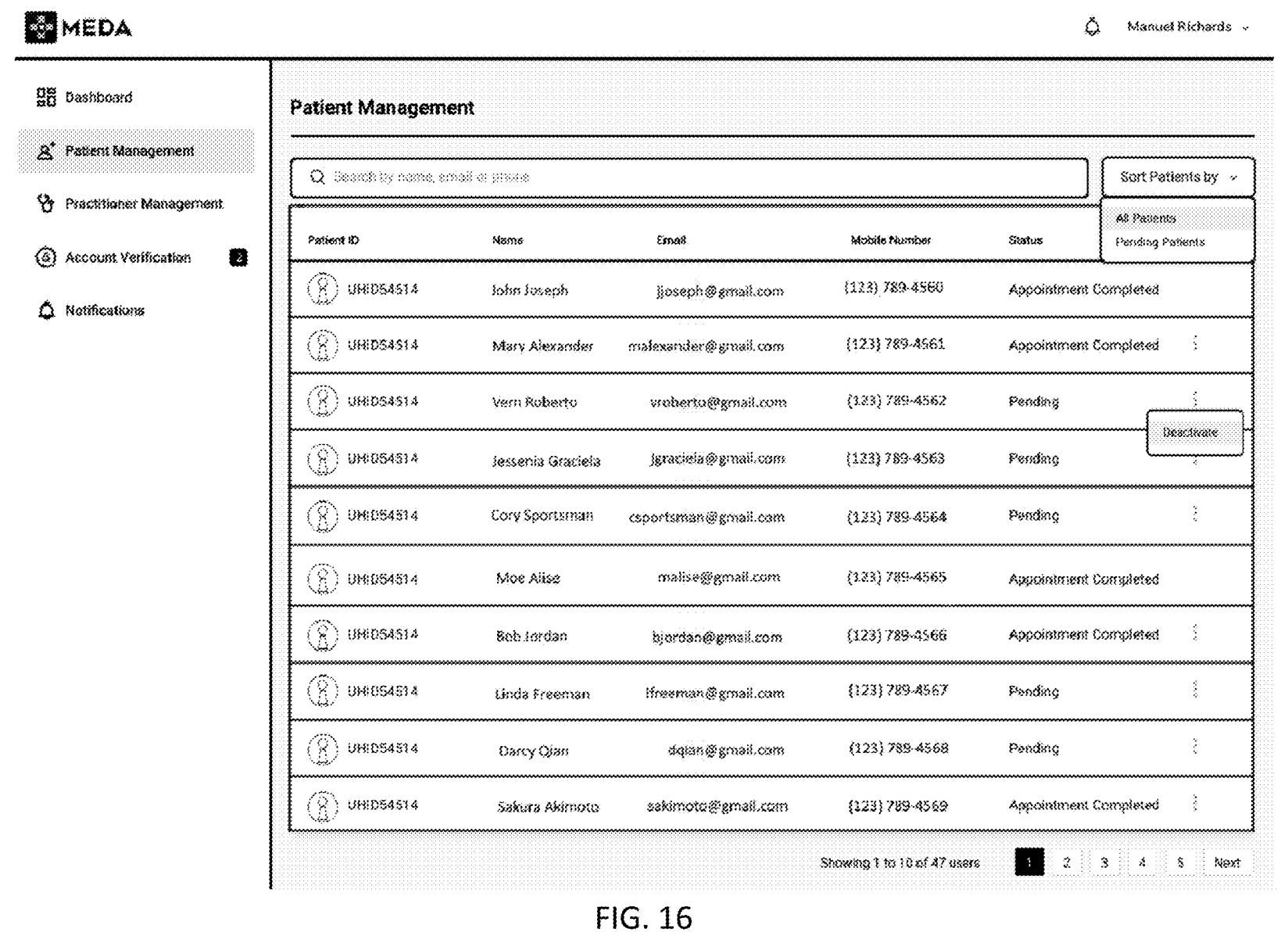

FIG. 16 is a patient management page for an administrator GUI according to one embodiment of the present invention. The patient management page includes a list of all patients associated with any practitioner profile that is, itself, associated with the administrator profile. This allows the administrator to monitor patients going through the hospital system, which is especially for, for example, billing. In one embodiment, the patient management page on the administrator GUI includes less information than the patient management patient on the practitioner GUI (e.g., does not show test results or medical history) for improved privacy. In one embodiment, the list of patients includes a patient identification number, a name, at least one email address, at least one phone number, at least one associated practitioner, and/or at least one status (e.g., appointment completed, pending, appointment upcoming, paid, not paid, etc.).

Figure 17:
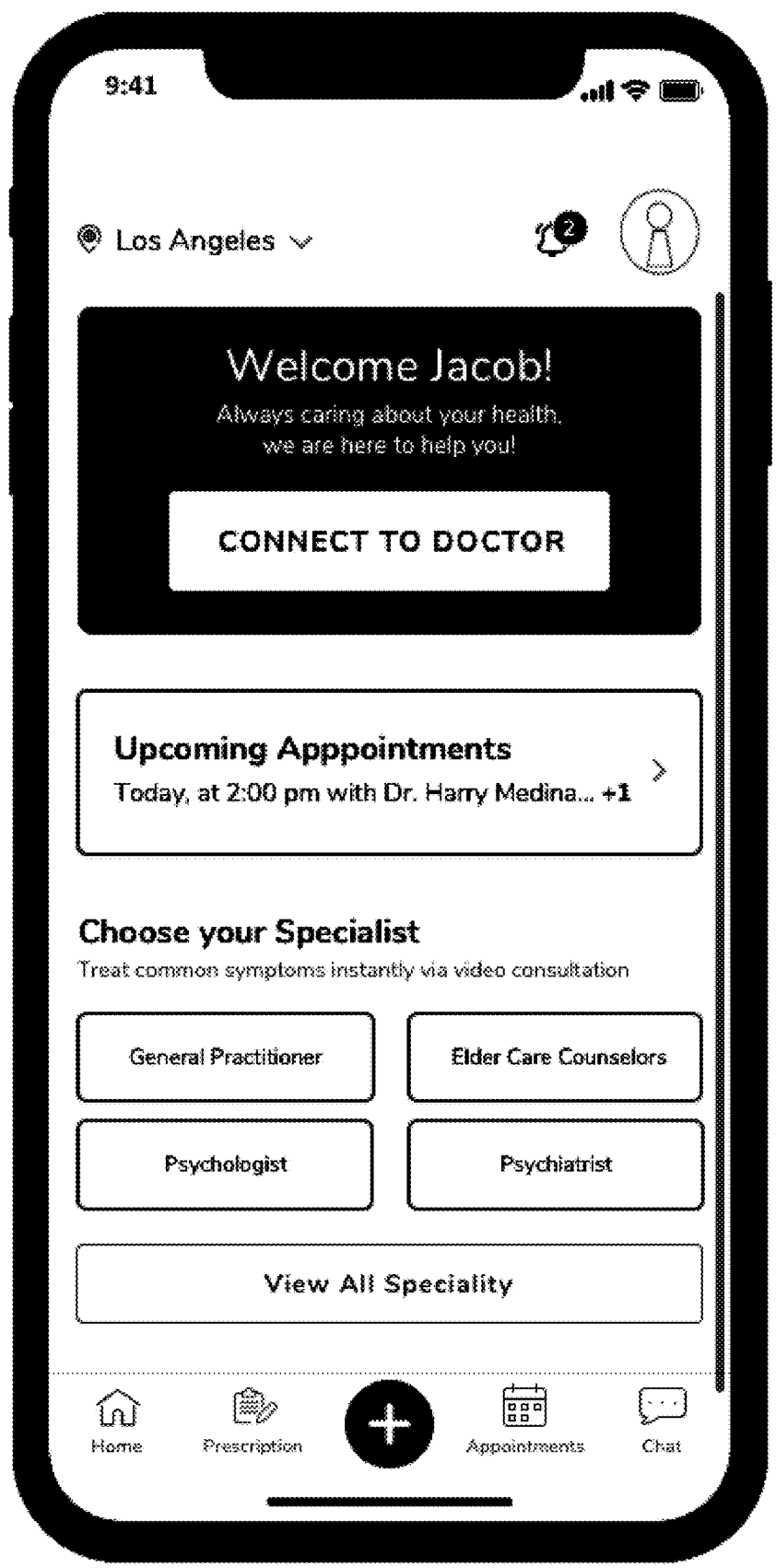
FIG. 17 illustrates a home dashboard page for a patient GUI according to one embodiment of the present invention.

FIG. 17 illustrates a home dashboard page for a patient GUI according to one embodiment of the present invention. The patient GUI provides a way for patients to quickly interact with specialists to receive treatment, to managing scheduling, to review results of appointments (e.g., check prescriptions, check test results, etc.), and to pay bills. In one embodiment, the platform automatically detects a location of at least one user device accessing the patient GUI in order to better match the patient with a physician in the local area. In one embodiment, the home dashboard page includes reminders of upcoming appointments, an option to search for available physicians, and/or an option to select a particular type of specialist to address the patient's current needs.

Figure 18:
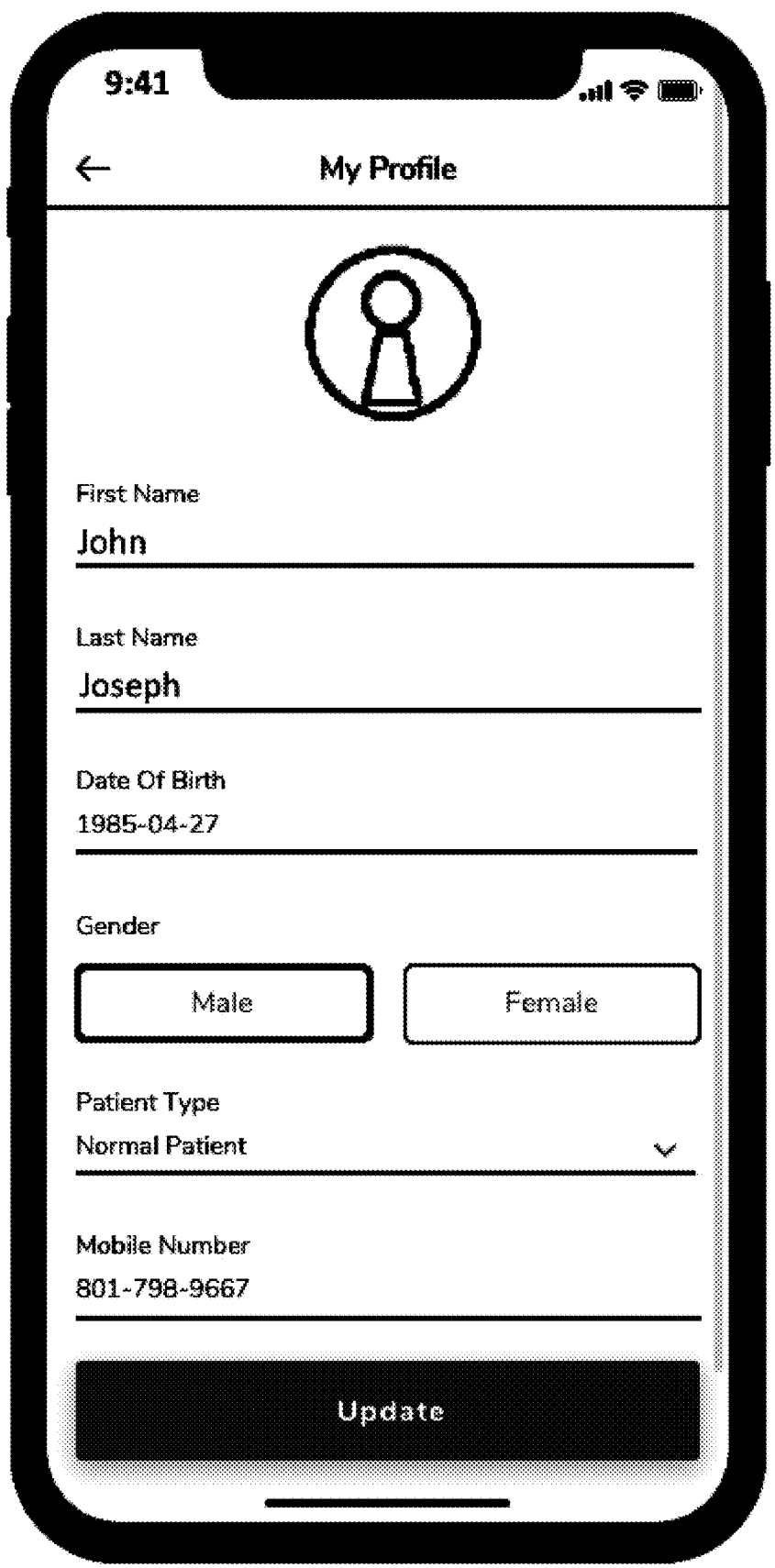
FIG. 18 illustrates a profile management page for a patient GUI according to one embodiment of the present invention.

FIG. 18 illustrates a profile management page for a patient GUI according to one embodiment of the present invention. The profile management page enables patients to edit personal details regarding of the patient profile, including, but not limited to, a first name, a middle name, a last name, a date-of-birth, a gender, a patient type, at least one mobile number, at least one email address, at least one home address, at least one payment method (e.g., at least one credit card, at least one checking account, at least one wire transfer method, etc.), and/or other personal information.

Figure 19:
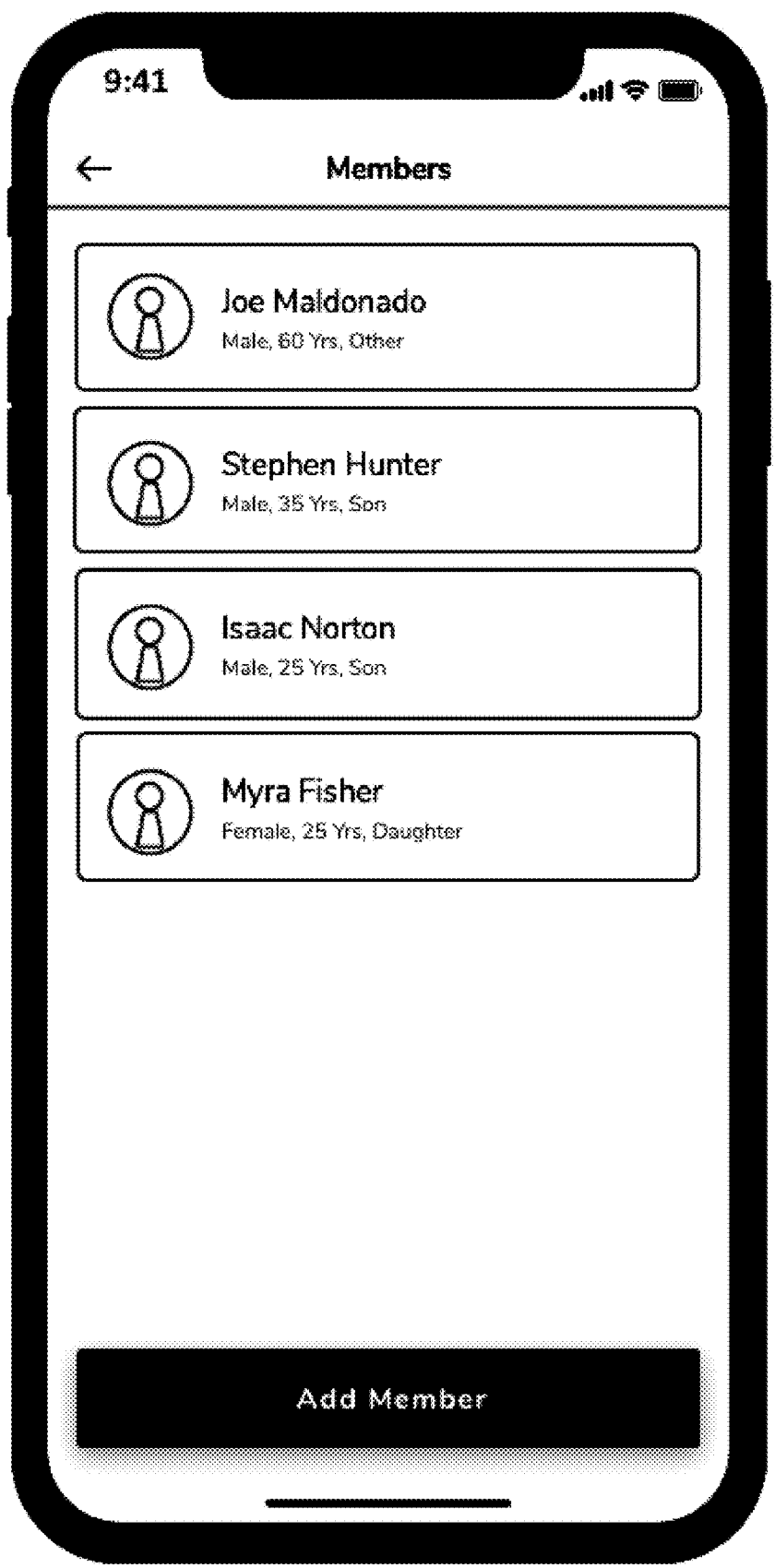
FIG. 19 illustrates a members management page for a patient GUI according to one embodiment of the present invention.

FIG. 19 illustrates a members management page for a patient GUI according to one embodiment of the present invention. In one embodiment, a patient profile includes more than one associated patient. This allows, for example, a single member of a household or family to manage the appointments of other members. In one embodiment, each patient profile includes a single main member and is limited to viewing test results, medical history, and/or other sensitive information regarding the single main member. In another embodiment, patient profiles are not limited to the information they are capable of receiving regarding constituent members. The members management page includes a list of members associated with the patient profile, including, by way of example and not limitation, a name of each member, an age of each member, a gender of each member, a profile picture of each member, and/or a relationship with each member.

Figure 20:
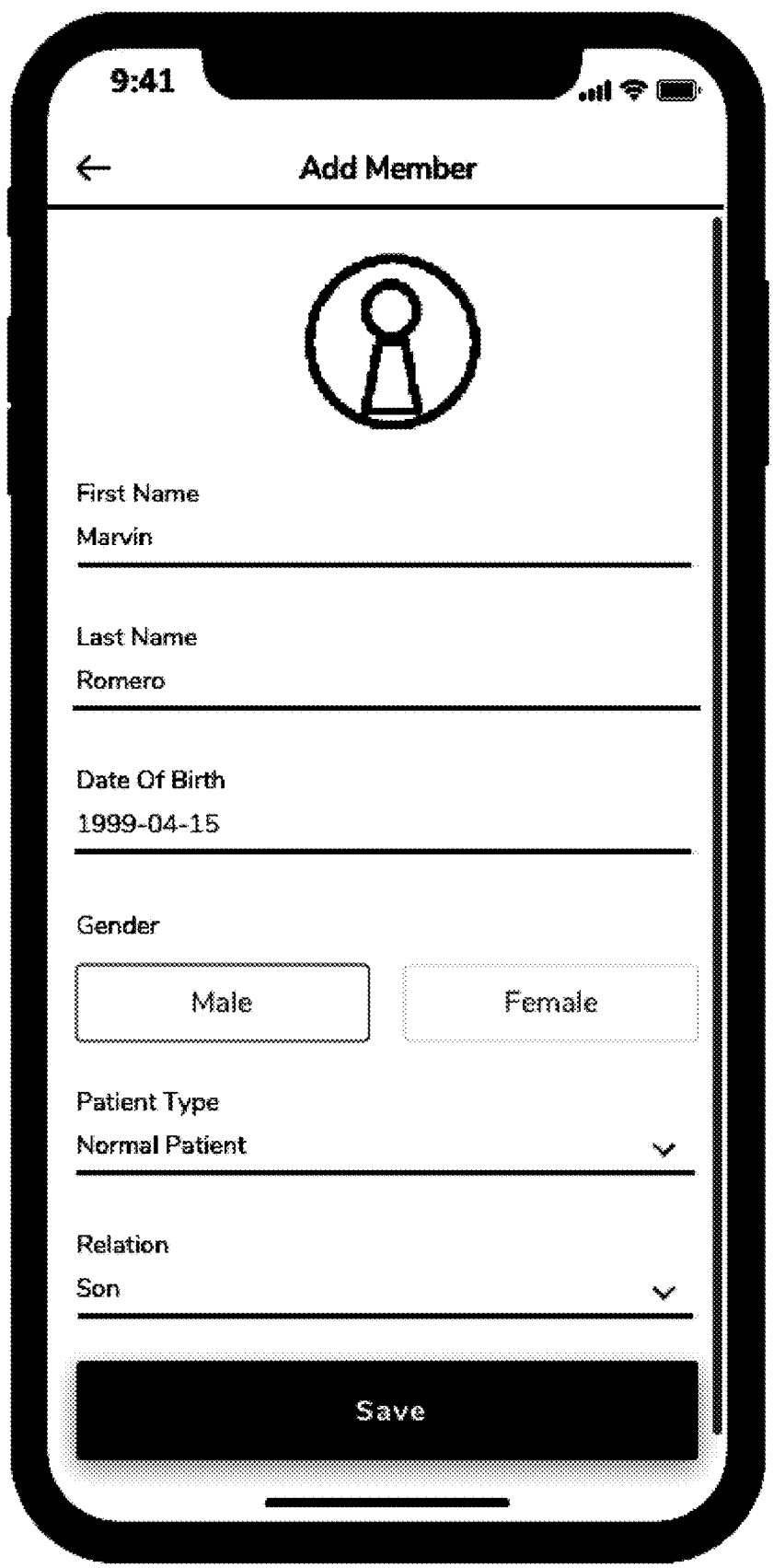
FIG. 20 illustrates an add member page for a patient GUI according to one embodiment of the present invention.

FIG. 20 illustrates an add member page for a patient GUI according to one embodiment of the present invention. The add member page of the patient GUI allows a patient profile to associate with additional members in order to more effectively manage those members schedules. In one embodiment, the add member page receives an input from a user device of a first name, a middle name, a last name, a date-of-birth, a gender, a patient type, a relationship, at least one email address, at least one phone number, an age, a profile picture, and/or other identifying information (e.g., SSN, driver's license number, etc.). In one embodiment, after receiving the information, the platform automatically transmits a confirmation message to at least one contact method associated with the member to be added (e.g., an email, an automated call, a text, etc.) requesting additional confirming documentation be transmitted to the platform in order to complete association of the new member with the patient profile. In one embodiment, the platform then receives confirming documentation (e.g., confirmation of SSN or other identifying information, and/or images of identification cards, such as driver's licenses) from the new member. The confirming documentation is then verified, automatically and/or manually, before the member is added to the patient profile.

Figure 21:
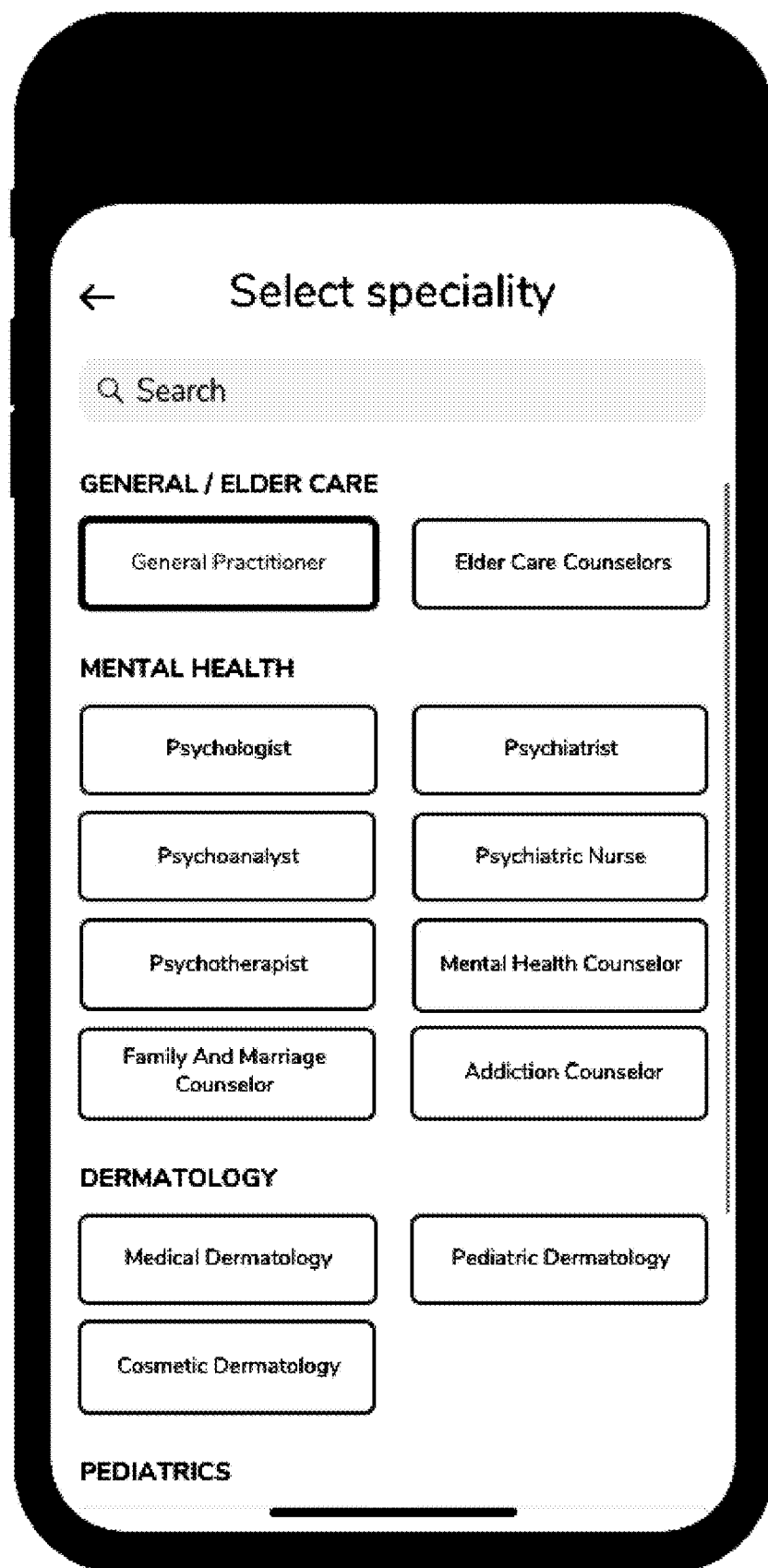
FIG. 21 illustrates a specialty selection page for a patient GUI according to one embodiment of the present invention.

FIG. 21 illustrates a specialty selection page for a patient GUI according to one embodiment of the present invention. Frequently, patients are looking for a particular type of physician (e.g., dermatologist, earth-nose-throat (ENT) physician, radiologist, podiatrist, obstetrician-gynecologists (OBGYNs), etc.), therapist, and/or counselor (e.g., psychologist, psychiatrist, psychoanalyst, psychiatric nurse, psychotherapist, mental health counselor, family counselor, marriage counselor, addiction counselor, etc.), rather than a general practitioner. The specialty selection page, therefore, allows the platform to receive inputs from the user device of a specific type of physician or other type of specialist that has available to see the patient. Alternatively, the platform is able to receive a selection to search for a general practitioner instead.

Figure 22:
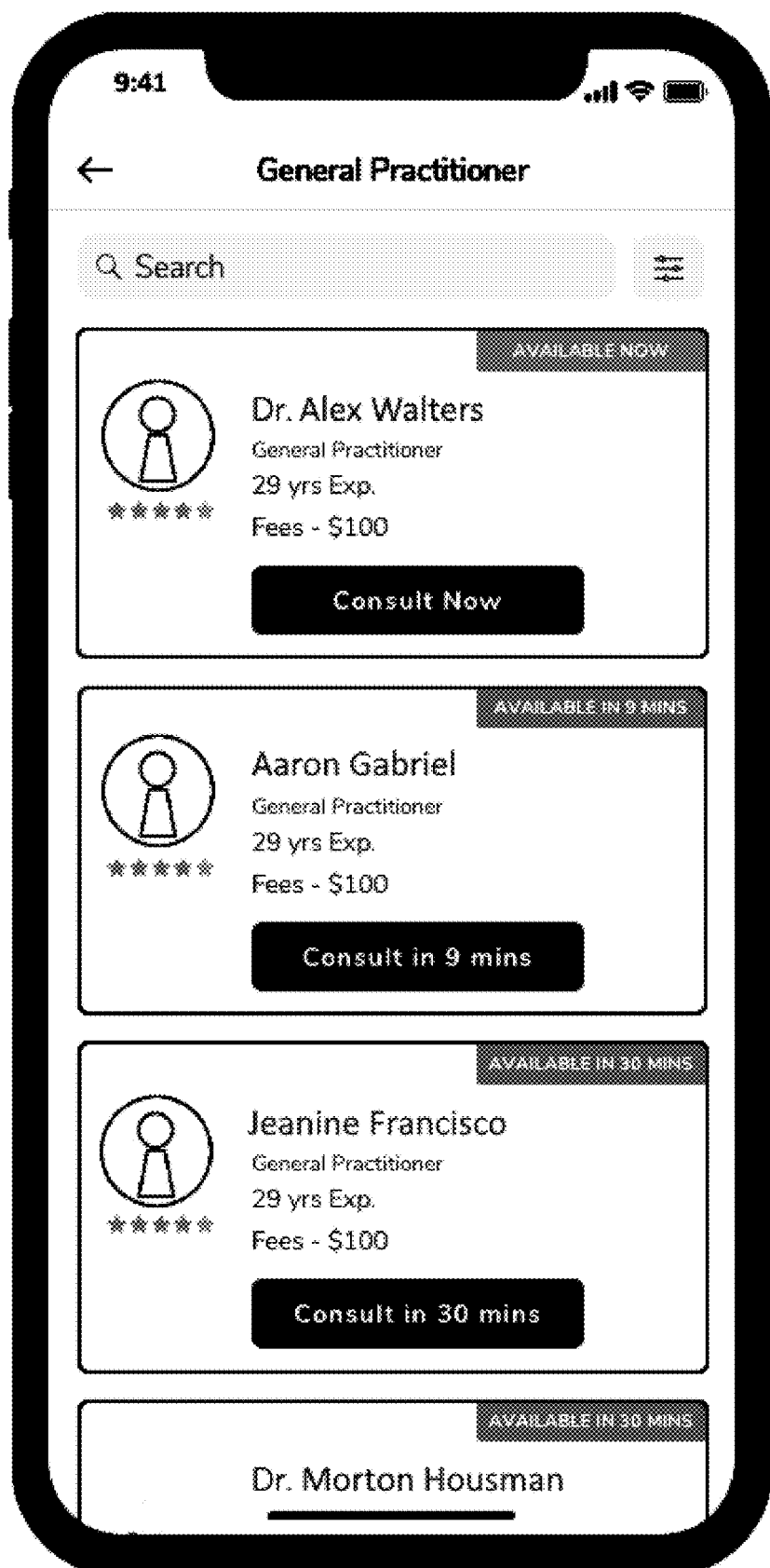
FIG. 22 illustrates a practitioner selection page for a patient GUI according to one embodiment of the present invention.

FIG. 22 illustrates a practitioner selection page for a patient GUI according to one embodiment of the present invention. After receiving a selection of a physician type, the platform automatically generates a list of physicians based on availability (e.g., how much time until the next available opening), consultation price, average rating, distance to the patient's location, patient profile preferences (e.g., max consultation price, whitelist and/or blacklist for specific physicians, restrictions on specific hospitals, etc.), and/or other factors. In one embodiment, the list of physicians includes name of each physician, a physician type for each physician, an amount of experience (e.g., number of years) for each physician, a profile picture for each physician, an average rating (e.g., a star rating) for each physician, a consultation price for each physician, and/or an availability for each physician (e.g., how long until the next available appointment). In one embodiment, through the practitioner selection page, the platform is able to receive a selection of a physician and, after receiving a selection, automatically connects the patient with the physician or puts the patient in a queue to speak with the physician. In one embodiment, the list of physicians includes an option for a consultation with one or more virtual (i.e., AI-generated) physicians.

Figure 23:
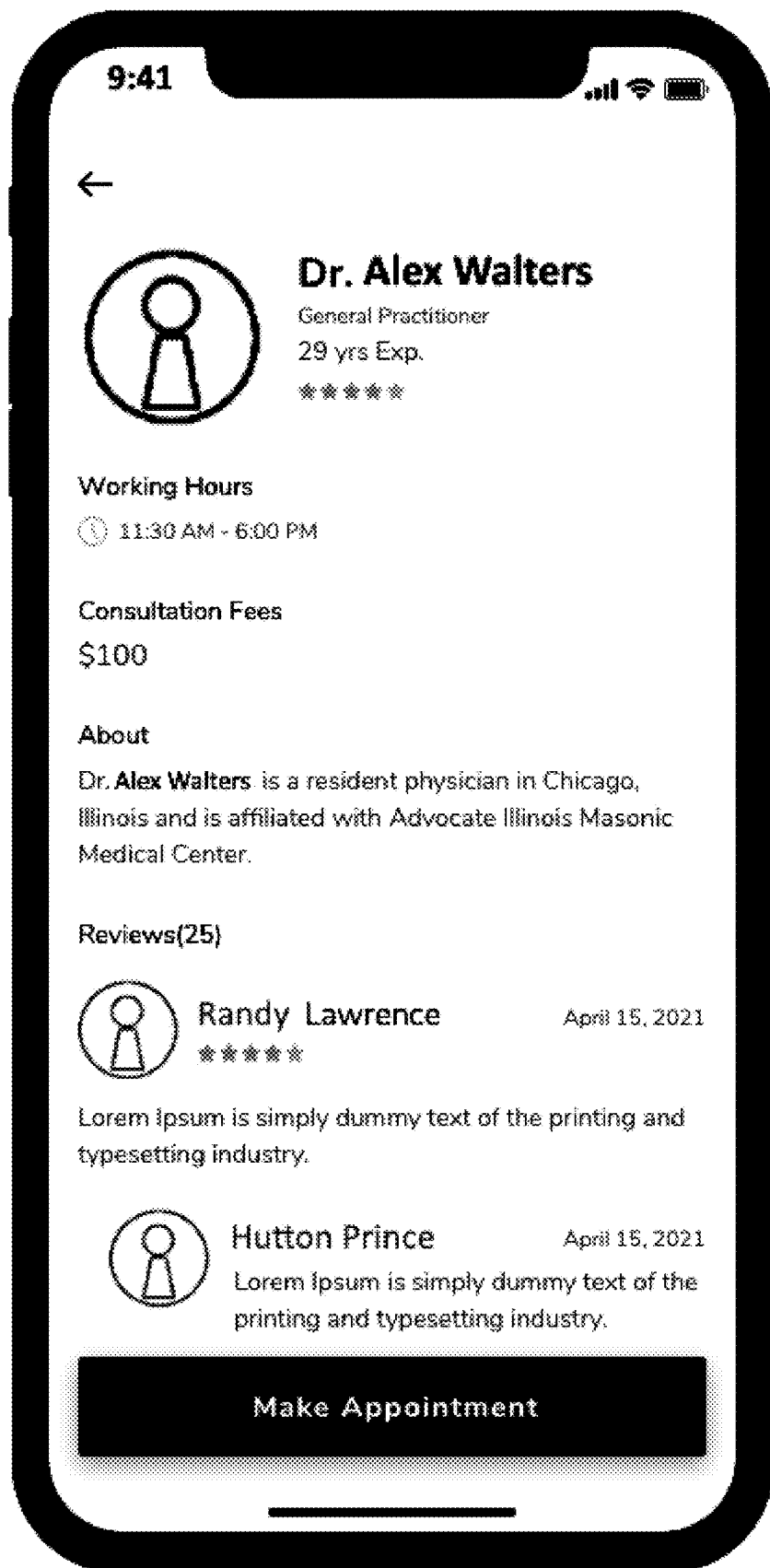
FIG. 23 illustrates a practitioner details page for a patient GUI according to one embodiment of the present invention.

FIG. 23 illustrates a practitioner details page for a patient GUI according to one embodiment of the present invention. The practitioner details page provides information regarding a practitioner, including reviews, such that a patient is able to make more informed decisions regarding whether to use a particular practitioner. In one embodiment, the practitioner details page includes a name, a profile picture, an amount of experience (e.g., number of years), normal working hours, a standard consultation fee, an average rating (e.g., a star rating), a brief description, and/or reviews from other patients of the practitioner. In one embodiment, through the practitioner details page, the platform is able to receive a selection to make an appointment with the practitioner, generating the practitioner appointment scheduling page.

Figure 24:
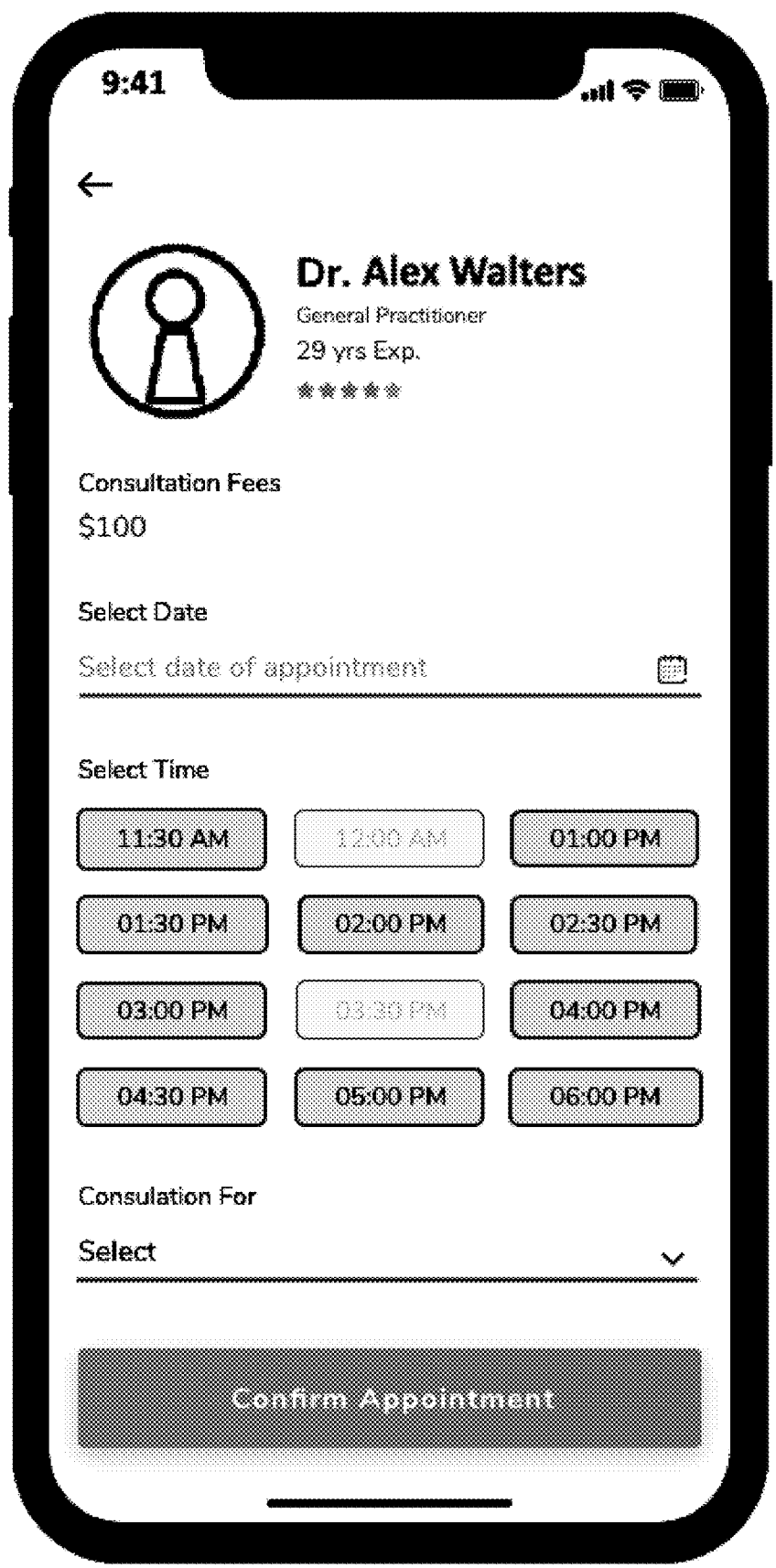
FIG. 24 illustrates a practitioner appointment scheduling page for a patient GUI according to one embodiment of the present invention.

FIG. 24 illustrates a practitioner appointment scheduling page for a patient GUI according to one embodiment of the present invention. Through the practitioner appointment scheduling page, the platform is operable to receive a selection of a time slot for an appointment from a user device associated with the patient profile. In one embodiment, the list of available times is set by the practitioner profile. In one embodiment, when a time is already booked for an appointment or a meeting, the platform automatically prevents selection of that time. In one embodiment, the platform receives a selection of a purpose for the appointment (e.g., annual physical, prescription refill, specific illness, etc.).

Figure 25:
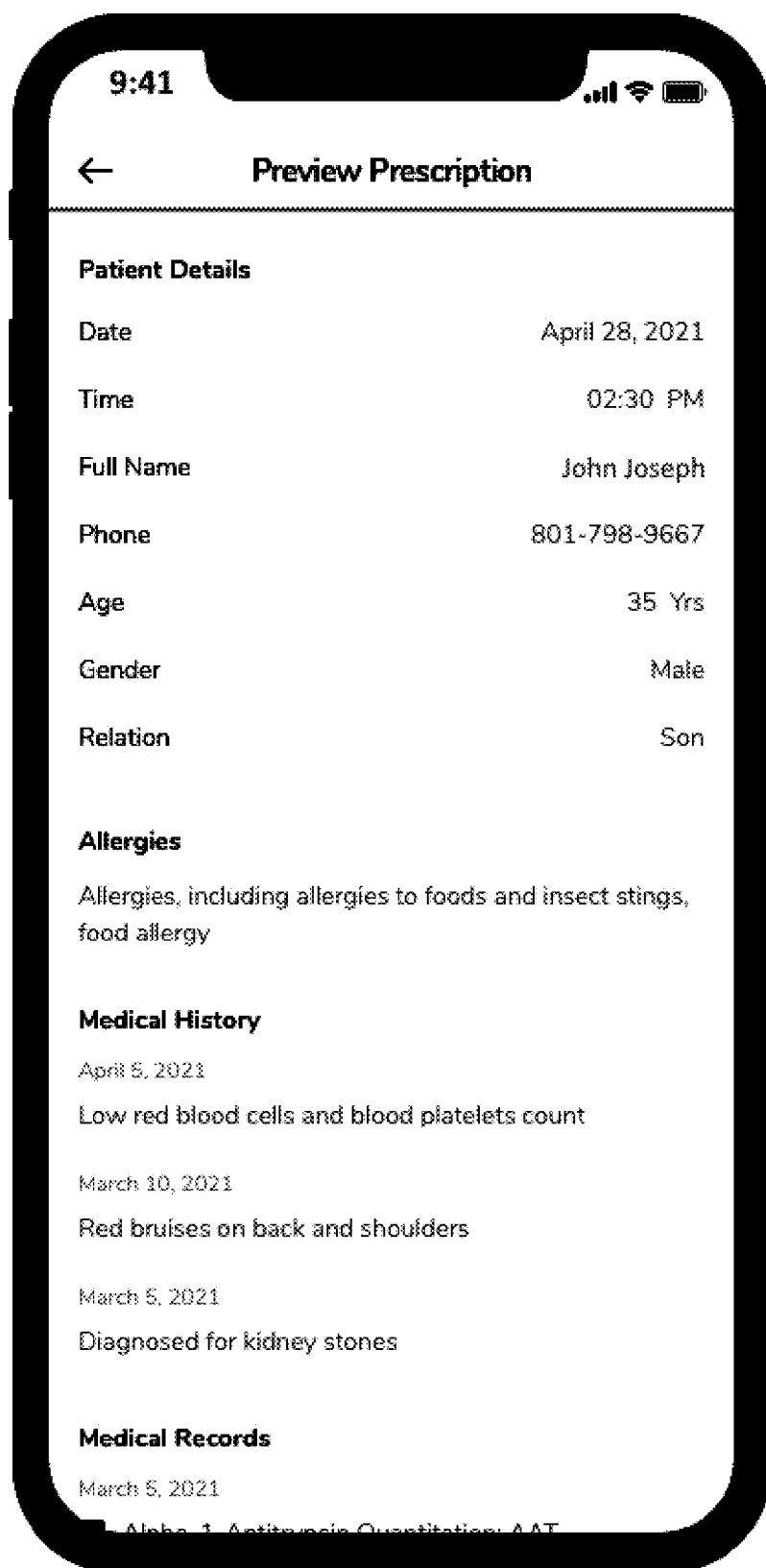
FIG. 25 illustrates a prescription details page for a patient GUI according to one embodiment of the present invention.

FIG. 25 illustrates a prescription details page for a patient GUI according to one embodiment of the present invention. The prescription details page is useful for the patient, as it allows the details of the prescription to be viewed, including, but not limited to, personal information about the patient, information regarding a recent appointment, the name of the prescription, the dosage of the prescription, where to pick up the prescription, how to take the prescription, warnings regarding the prescription, and/or potential side effects of the prescription. The prescription details page is useful as it provides not only information regarding the actual prescription, but also context of the physician's observations of the patient from an appointment that led to the prescription.

Figure 26:
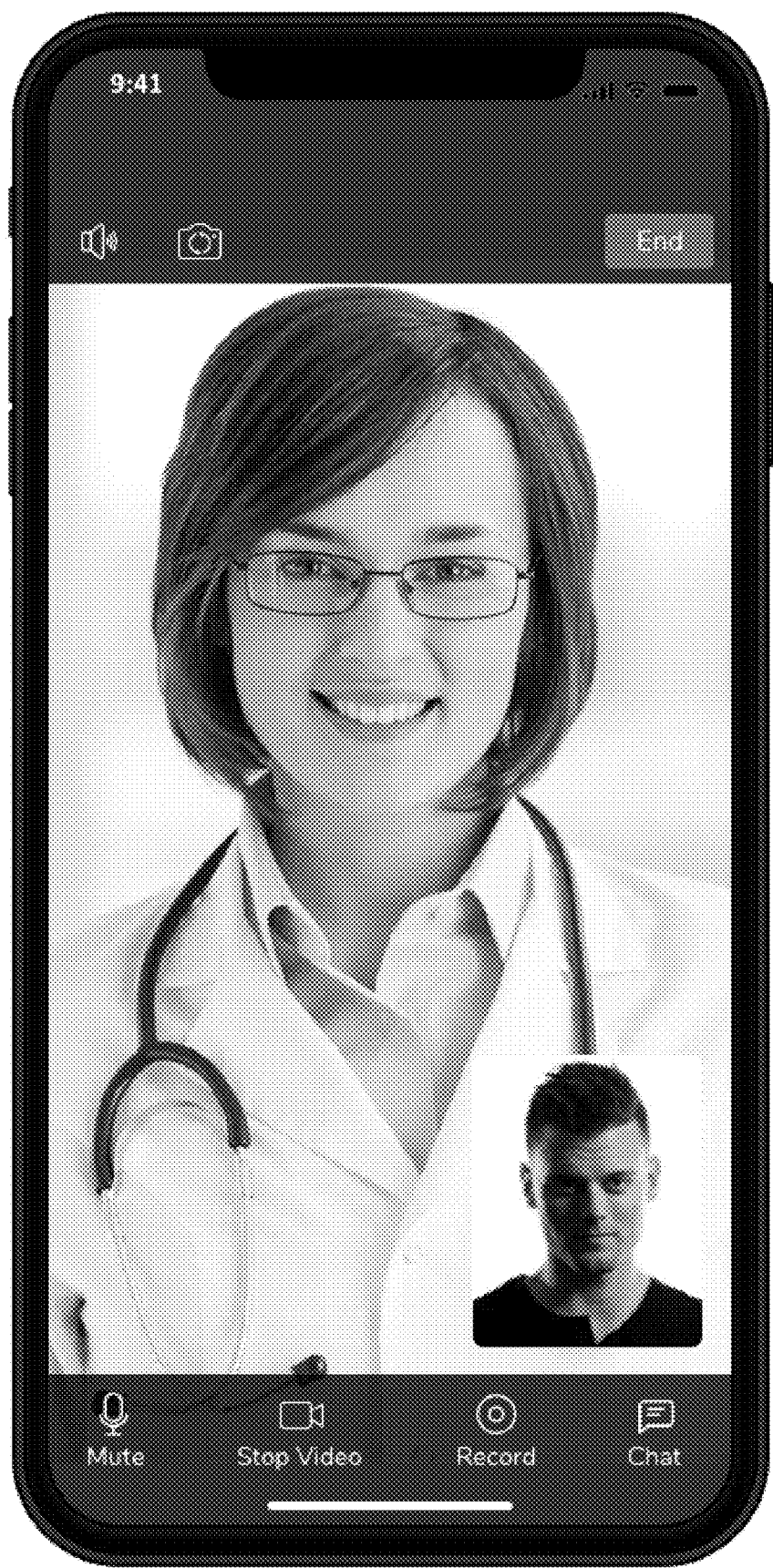
FIG. 26 illustrates a video chat interface according to one embodiment of the present invention.

FIG. 26 illustrates a video chat interface according to one embodiment of the present invention. The platform is operable to facilitate a video chat between patients and practitioners (or between two practitioners). In one embodiment, the video chat interface is able to receive selections to mute the audio coming from a user's device, stop the video coming from a user's device, record the conversation, flip the camera (from a front camera of the user device to a back camera of the user or vice versa), mute the audio from the other user, begin a text conversation, and/or end the conversation.

The patient interface of the telemedicine platform includes a virtual assistant, or an artificial human doctor. The platform receives messages text messages and/or audio messages (which are then translated into text using natural language processing) from at least one user device. Systems and methods for natural language processing able to be used with the present invention include, but are not limited to, those described in U.S. Pat. No. 10,482,184, which is incorporated herein by reference in its entirety. In one embodiment, the messages include information including, but not limited to, personal information regarding a patient, a description of symptoms, a description of desired treatment, one or more qualities of a required physician, and/or other health information or preferences. The platform then automatically generates a response to the patient, including, for example, an acknowledgment of the messages transmitted by the user device and/or further inquiries for additional information. In one embodiment, the platform receives a selection of ethnicity, gender, language, dialect, and/or accent for the virtual assistant. One of ordinary skill in the art will understand that the number of languages able to understood are not intended to be limiting and the number of languages able to be used in a response are not intended to be limiting. Possible languages include, but are not limited to, English, Spanish, French, Italian, Mandarin Chinese, Cantonese, Japanese, Hindi, Urdu, Arabic, Swahili, Korean, Portuguese, German, Luxembourgish, Swedish, Norwegian, Danish, Finnish, Russian, Ukrainian, Icelandic, Dutch, Polish, Slovak, Serbo-Croatian, Bosnian, Albanian, Greek, Romanian, Bulgarian, Slovene, Czech, Romansch, Occitan, Lithuanian, Latvian, Estonian, Hungarian, Turkish, Hebrew, Armenian, Georgian, Azeri, Farsi, Pashto, Kazakh, Uzbek, Turkmen, Tajik, Kyrgyz, Tibetan, Mongolian, Yue Chinese, Wu Chinese, Hakka Chinese, Jinyu Chinese, Bengali, Marathi, Punjabi, Gujarati, Odia, Bhojpuri, Malayalam, Maithili, Tamil, Sindhi, Sinhala, Assamese, Nepali, Indonesian, Javanese, Sundanese, Thai, Vietnamese, Lao, Khmer, Burmese, Tagalog, Cebuano, Kannada, Amharic, Somali, Afrikaans, Xhosa, Zulu, Shona, Igbo, Yoruba, Hausa, Kikuyu, and/or any other language (including individual dialects and creole languages).

In one embodiment, the automatically generated response by the virtual assistant includes text messages sent to the at least one user device. Systems and methods for automatic integration of a virtual assistant and artificial intelligence include, but are not limited to, U.S. Pat. No. 11,302,332, which is incorporated herein by reference in its entirety.

In one embodiment, the virtual assistant is able to be generated and placed into an augmented reality (AR) environment.

Figure 27:
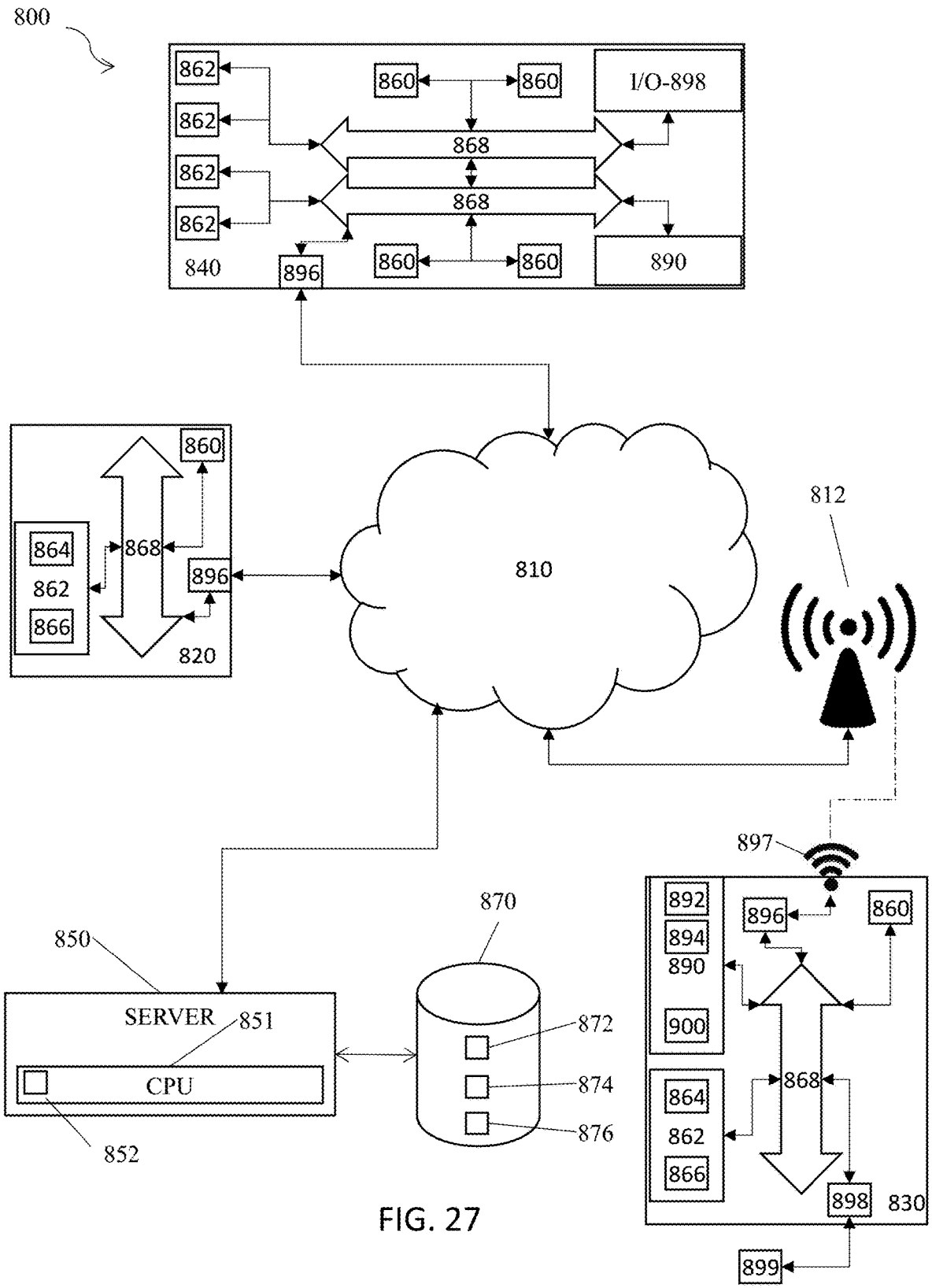
FIG. 27 is a schematic diagram of a system of the present invention.

FIG. 27 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 27, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 27, is operable to include other components that are not explicitly shown in FIG. 27, or is operable to utilize an architecture completely different than that shown in FIG. 27. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The platform is operable to utilize a plurality of learning techniques including, but not limited to, machine learning (ML), artificial intelligence (AI), deep learning (DL), neural networks (NNs), artificial neural networks (ANNs), support vector machines (SVMs), Markov decision process (MDP), and/or natural language processing (NLP). The platform is operable to use any of the aforementioned learning techniques alone or in combination.

Further, the platform is operable to utilize predictive analytics techniques including, but not limited to, machine learning (ML), artificial intelligence (AI), neural networks (NNs) (e.g., long short term memory (LSTM) neural networks), deep learning, historical data, and/or data mining to make future predictions and/or models. The platform is preferably operable to recommend and/or perform actions based on historical data, external data sources, ML, AI, NNs, and/or other learning techniques. The platform is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. A telemedicine system, comprising:
   at least one server, including a processor and a memory, and at least one database;
   wherein the at least one server is in network communication with at least one patient user device and at least one practitioner device;
   wherein the at least one server generates at least one patient profile corresponding to the at least one patient user device;
   wherein one or more of the at least one patient profile includes a plurality of members, and wherein the at least one patient profile manages scheduling for appointments of each of the plurality of members;
   wherein at least one contact method associated with at least one member of a plurality of members and an indication of a relationship between the at least one member and the at least one patient profile are input to the at least one patient profile;
   wherein a confirmation message is transmitted to the at least one member via the at least one contact method associated with the at least one member;
   wherein the confirmation message includes a request for additional documentation for completion of the addition of the at least one member to the at least one patient profile;
   wherein the at least one practitioner device is operable to manage availability of at least one practitioner profile by receiving a time range selection by click selection of a circle at a start point representing a start time of the time range and drag selection of the circle to an end point representing an end time of the time range;
   wherein an area covered by the time range selection represents availability of the at least one practitioner profile;
   wherein the at least one server includes an artificial intelligence module;
   wherein the artificial intelligence module receives messages from the at least one patient user device and automatically detects described symptoms and provides a list of suggested healthcare providers to the at least one patient user device based on natural language processing of the messages and a predictive diagnosis of a medical concern based on the described symptoms, wherein the list of suggested healthcare providers specialize in treatment of the medical concern;
   wherein the artificial intelligence module automatically uses natural language processing to analyze the messages received from the at least one user device and generates a list of International Classification of Diseases (ICD)-10 diagnosis codes based on the messages;
   wherein the list of suggested healthcare providers includes a profile picture and a quantification of experience associated with a practitioner associated with the at least one practitioner profile;
   wherein the artificial intelligence module automatically generates responses to the messages from the at least one patient user device to prompt for further information;
   wherein the system is operable to receive a selection by the at least one patient user device for at least one real physician or at least one artificial intelligence generated physician to solely host a consultation; and
   wherein the artificial intelligence module generates an animated human face and animates the animated human face to synchronize lip movements to audio of the automatically generated responses, wherein the server receives a selection of a gender and/or ethnicity for the animated human face and an accent and/or dialect for the audio of the automatically generated response, wherein the gender and/or ethnicity of the animated human face and the accent and/or dialect of the audio of the automatically generated response corresponds to the selected gender and/or ethnicity and accent and/or dialect.

2. The system of claim 1, wherein the at least one server receives a selection to filter the list of suggested healthcare providers to only display one or more specific types of healthcare providers.

3. The system of claim 1, wherein the list of suggested healthcare providers is based on a geolocation of the at least one patient user device, consultation prices for different healthcare providers, estimated time until an available consultation with each healthcare provider, and/or average ratings of healthcare providers.

4. The system of claim 1, wherein the artificial intelligence module automatically diagnoses a patient based on at least one description of symptoms, patient demographic data, at least one test result, and/or at least one scan.

5. The system of claim 1, wherein the at least one server receives prescription instructions from the at least one practitioner device and transmits the prescription instructions to at least one pharmacy.

6. The system of claim 1, wherein the at least one server automatically updates an electronic medical record corresponding to the at least one patient profile based on results of each consultation.

7. The system of claim 1, wherein the at least one server includes an integrated billing module, wherein the integrated billing module displays at least one cost associated with a patient profile before and after insurance.

8. The system of claim 1, wherein the artificial intelligence module receives at least one image from the at least one patient user device and generates a diagnosis based on analysis of the at least one image.

9. A telemedicine system, comprising:
at least one server, including a processor and a memory, and at least one database;
wherein the at least one server is in network communication with at least one patient user device and at least one practitioner device;
wherein the at least one server includes an artificial intelligence module;
wherein the artificial intelligence module receives messages from the at least one patient user device and automatically detects described symptoms and/or provides a list of suggested healthcare providers to the at least one patient user device based on natural language processing of the messages;
wherein the artificial intelligence module automatically uses natural language processing to analyze the messages received from the at least one user device and generates a list of International Classification of Diseases (ICD)-10 diagnosis codes based on the messages;
wherein the artificial intelligence module automatically generates responses to the messages from the at least one patient user device to prompt for further information;
wherein the artificial intelligence module generates audio of the automatically generated responses and transmits the audio to the at least one patient user device;
wherein the list of suggested healthcare providers is based on a geolocation of the at least one patient user device, consultation prices for different healthcare providers, estimated time until an available consultation, and/or average ratings of healthcare providers;
wherein the at least one server generates at least one patient profile corresponding to the at least one patient user device and at least one practitioner profile corresponding to the at least one practitioner device;
wherein the at least one server generates a chat portal between the at least one patient profile and the at least one practitioner profile, wherein the chat portal includes search functionality to search for keywords in messages sent between the at least one patient profile and the at least one practitioner profile;
wherein the at least one practitioner profile includes at least one practitioner pager number and at least one patient details page, wherein the at least one patient details page includes an indication of a patient type, wherein the patient type includes an indication of a minor patient;
wherein the at least one practitioner profile is operable to deactivate the at least one patient profile, wherein deactivation of the at least one patient profile removes the at least one patient profile from association with the at least one practitioner profile;
wherein the at least one server tracks an amount of time spent in consultation by the at least one practitioner device;
wherein the at least one practitioner device is operable to manage availability of the at least one practitioner profile by receiving a time range selection by click selection of a circle at a start point representing a start time of the time range and drag selection of the circle to an end point representing an end time of the time range;
wherein an area covered by the time range selection represents availability of the at least one practitioner profile;
wherein the at least one server creates a log of the amount of time spent in consultation by the at least one practitioner device; and
wherein the at least one server is operable to offer a non-monetary incentive to the at least one practitioner profile based on the amount of time spent in consultation.

10. The system of claim 9, wherein the at least one server receives a selection to filter the list of suggested healthcare providers to one or more specific types of healthcare providers.

11. The system of claim 9, wherein the artificial intelligence module receives at least one image from the at least one patient user device and generates a diagnosis based on analysis of the at least one image.

12. The system of claim 9, wherein the at least one server receives a selection from the at least one patient user device of a language for the audio of the automatically generated responses.

13. The system of claim 9, wherein the at least one server receives prescription instructions from the at least one practitioner device and transmits the prescription instructions to at least one pharmacy.

14. The system of claim 9, wherein the at least one server automatically updates an electronic medical record corresponding to the at least one patient profile based on results of each consultation.

15. The system of claim 9, wherein one or more of the at least one patient profile includes a plurality of members, and wherein the at least one patient profile manages scheduling for appointments of each of the plurality of members.

16. A telemedicine system, comprising:
at least one server, including a processor and a memory, and at least one database;
wherein the at least one server is in network communication with at least one patient user device and at least one practitioner device;
wherein the at least one server generates at least one patient profile corresponding to the at least one patient user device and at least one practitioner profile corresponding to the at least one practitioner device,
wherein the at least one server receives a selection of available consultation times from the at least one practitioner device;

wherein the at least one server automatically updates the selection of available consultation times when appointments are made;

wherein the at least one server includes an artificial intelligence module;

wherein the artificial intelligence module receives messages from the at least one patient user device and automatically detects described symptoms and/or provides a list of suggested healthcare providers to the at least one patient user device based on natural language processing of the messages;

wherein the artificial intelligence module automatically uses natural language processing to analyze the messages received from the at least one user device and generates a list of International Classification of Diseases (ICD)-10 diagnosis codes based on the messages;

wherein the list of suggested healthcare providers includes a profile picture and a quantification of experience associated with a practitioner associated with the at least one practitioner profile;

wherein the artificial intelligence module automatically generates responses to the messages from the at least one patient user device to prompt for further information;

wherein the artificial intelligence module generates audio of the automatically generated responses and transmits the audio to the at least one patient user device; and wherein the artificial intelligence module receives a selection of a dialect from the at least one patient user device, wherein the audio of the automatically generated responses corresponds to the selected dialect.

17. The system of claim 16, wherein the at least one server receives a selection to filter the list of suggested healthcare providers to one or more specific types of healthcare providers.

18. The system of claim 16, wherein the list of suggested healthcare providers is based on a geolocation of the at least one patient user device, consultation prices for different healthcare providers, estimated time until an available consultation, and/or average ratings of healthcare providers.

19. The system of claim 16, wherein the at least one server is in network communication with at least one administrator device, wherein the at least one server generates at least one administrator profile corresponding to the at least one administrator device, wherein the at least one administrator profile includes at least one practitioner management page and at least one patient management page.

20. The system of claim 16, wherein the at least one server receives prescription instructions from the at least one practitioner device and transmits the prescription instructions to at least one pharmacy.

* * * * *